US012420010B2

(12) United States Patent
Scheurer et al.

(10) Patent No.: US 12,420,010 B2
(45) Date of Patent: Sep. 23, 2025

(54) NEEDLE INSERTION AND RETRACTION MECHANISM

(71) Applicant: Ypsomed AG, Burgdorf (CH)

(72) Inventors: Simon Scheurer, Bern (CH); Christian Schrul, Burgdorf (CH); Stefan Burren, Schwarzenburg (CH); Mario Bernhard, Burgdorf (CH); Jürg Hirschel, Bern (CH)

(73) Assignee: Ypsomed AG, Burgdorf (CH)

( * ) Notice: Subject to any disclaimer, the term of this patent is extended or adjusted under 35 U.S.C. 154(b) by 1166 days.

(21) Appl. No.: 17/149,347

(22) Filed: Jan. 14, 2021

(65) Prior Publication Data

US 2021/0138151 A1 May 13, 2021

Related U.S. Application Data

(63) Continuation of application No. PCT/IB2019/055544, filed on Jul. 1, 2019.

(30) Foreign Application Priority Data

Jul. 30, 2018 (EP) ...................................... 18186224

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 2005/1583* (2013.01);
(Continued)

(58) Field of Classification Search
CPC .... A61M 5/14248; A61M 2005/14252; A61M 5/158; A61M 5/162; A61M 2005/1585;
(Continued)

(56) References Cited

U.S. PATENT DOCUMENTS 6,474,219 B2  11/2002  Klitmose et al.
9,107,999 B2   8/2015  Moberg et al.
(Continued)

FOREIGN PATENT DOCUMENTS

DE   102004059491 A1   7/2006
EP       3260149 A1  12/2017
(Continued)

OTHER PUBLICATIONS

International Preliminary Report on Patentability issued in International Application No. PCT/EP2020/079537, mailed on May 6, 2022, 9 pages.
(Continued)

*Primary Examiner* — Michael J Tsai
*Assistant Examiner* — Kathleen Paige Farrell
(74) *Attorney, Agent, or Firm* — Dorsey & Whitney LLP

(57) ABSTRACT

A needle insertion and retraction mechanism for a medication delivery device includes a housing and a needle carrier holding a needle guided by the housing and moved along a needle axis. A first spring member is adapted to move the carrier in an insertion direction. A second spring member is adapted to retract the carrier in a retraction direction, opposite the insertion direction. A control element, linearly guided by the housing, moves transversely to the needle axis from a starting position, via a needle insertion release position, to a needle retraction release position. When the control element is in its starting position, the control element is coupled to the carrier to prevent the carrier from moving in the insertion direction. When the control element is in the release position, the control element is decoupled from the carrier and the first spring member drives the carrier in the needle insertion direction.

17 Claims, 10 Drawing Sheets

(52) U.S. Cl.
CPC .............. *A61M 2005/1585* (2013.01); *A61M 2205/581* (2013.01); *A61M 2205/583* (2013.01); *A61M 2205/587* (2013.01); *A61M 2205/8206* (2013.01)

(58) Field of Classification Search
CPC .. A61M 2005/1583; A61 2005/2073; A61M 2005/206; A61M 2005/202; A61M 5/322; A61M 2005/3227; A61M 5/3234; A61M 2005/3235; A61M 2005/3236; A61M 2005/3238; A61M 2005/3239; A61M 5/2033; A61M 2005/1581; A61M 5/3287; A61M 2005/2474
See application file for complete search history.

(56) References Cited

U.S. PATENT DOCUMENTS

| | | | |
|---|---|---|---|
| 10,137,241 B2* | 11/2018 | Lanigan | A61M 5/142 |
| 2008/0051738 A1* | 2/2008 | Griffin et al. | A61M 5/14248 |
| 2009/0054866 A1* | 2/2009 | Teisen-Simony et al. | A61M 5/14248 |
| 2009/0093792 A1 | 4/2009 | Gross et al. | |
| 2009/0099521 A1* | 4/2009 | Gravesen | A61M 5/14248 604/136 |
| 2010/0063443 A1 | 3/2010 | Lin | |
| 2011/0166512 A1 | 7/2011 | Both et al. | |
| 2011/0306929 A1 | 12/2011 | Levesque et al. | |
| 2012/0035546 A1 | 2/2012 | Cabiri | |
| 2012/0123344 A1 | 5/2012 | Hornig et al. | |
| 2013/0006213 A1 | 1/2013 | Arnitz et al. | |
| 2013/0060233 A1 | 3/2013 | Oconnor et al. | |
| 2013/0253431 A1* | 9/2013 | Kaufmann | A61M 5/3287 604/157 |
| 2014/0163526 A1 | 6/2014 | Cabiri et al. | |
| 2016/0082182 A1* | 3/2016 | Gregory et al. | A61M 5/14248 |
| 2016/0184512 A1* | 6/2016 | Marbet et al. | A61M 5/14248 |
| 2016/0213837 A1* | 7/2016 | Schabbach et al. | A61M 5/158 |
| 2016/0256352 A1 | 9/2016 | Bar-El et al. | |
| 2016/0256353 A1 | 9/2016 | Bar-El et al. | |
| 2017/0100305 A1 | 4/2017 | Moia et al. | |
| 2017/0182303 A1* | 6/2017 | Tallarida et al. | A61M 5/158 |
| 2017/0326292 A1* | 11/2017 | Sage, Jr. et al. | A61M 5/14248 |
| 2017/0340837 A1* | 11/2017 | Nazzaro et al. | A61M 5/14248 |
| 2017/0354783 A1 | 12/2017 | Gazeley et al. | |
| 2018/0008769 A1 | 1/2018 | O'Connor et al. | |
| 2018/0028747 A1 | 2/2018 | Hanson et al. | |
| 2018/0117251 A1* | 5/2018 | Rioux et al. | A61M 5/2033 |
| 2018/0236173 A1 | 8/2018 | McCaffrey et al. | |
| 2019/0117880 A1 | 4/2019 | Hirschel et al. | |
| 2019/0160225 A1* | 5/2019 | Verlaak | A61M 5/14248 |
| 2020/0023122 A1 | 1/2020 | McCullough et al. | |
| 2020/0155759 A1 | 5/2020 | Hanson et al. | |
| 2022/0241497 A1 | 8/2022 | Burren et al. | |
| 2022/0362458 A1* | 11/2022 | Schrul et al. | A61M 5/14248 |

FOREIGN PATENT DOCUMENTS

| | | |
|---|---|---|
| EP | 3348284 A2 | 7/2018 |
| EP | 3067083 B1 | 12/2018 |
| EP | 3539592 A1 | 9/2019 |
| EP | 3603700 A1 | 2/2020 |
| EP | 3656419 A1 | 5/2020 |
| GB | 2552340 A | 1/2018 |
| WO | 9509021 A1 | 4/1995 |
| WO | 0183008 A1 | 11/2001 |
| WO | 0240083 A2 | 5/2002 |
| WO | 2004056411 A2 | 7/2004 |
| WO | 2005002649 A1 | 1/2005 |
| WO | 2006108809 A1 | 10/2006 |
| WO | 2007038059 A2 | 4/2007 |
| WO | 2010029054 A1 | 3/2010 |
| WO | 2011012465 A1 | 2/2011 |
| WO | 2011046850 A1 | 4/2011 |
| WO | 2011046950 A1 | 4/2011 |
| WO | 2013140395 A1 | 9/2013 |
| WO | 2015032747 A1 | 3/2015 |
| WO | 2016053954 A1 | 4/2016 |
| WO | 2017089286 A1 | 6/2017 |
| WO | 2017219154 A1 | 12/2017 |
| WO | 2017219155 A1 | 12/2017 |
| WO | 2018024625 A1 | 2/2018 |
| WO | 2020026049 A1 | 2/2020 |
| WO | 2021083746 A1 | 5/2021 |

OTHER PUBLICATIONS

International Preliminary Report on Patentability received for International Application No. PCT/IB2019/055544, mailed on Feb. 11, 2021, 7 pages.

Extended European Search Report issued in European Application No. 19206382.4, mailed on Mar. 24, 2020, 9 pages.

International Search Report and Written Opinion issued in International Patent Application No. PCT/EP2020/079537, issued on Jan. 18, 2021, 11 pages.

International Search Report and Written Opinion received for International Application No. PCT/IB2019/055544, mailed on Jul. 29, 2019, 9 pages.

Extended European Search Report received for European Patent Application No. 18186224.4, mailed on Nov. 9, 2018, 6 pages.

"Extended European Search Report", issued in EP16175887.5 on Dec. 23, 2016, 8 pages.

* cited by examiner

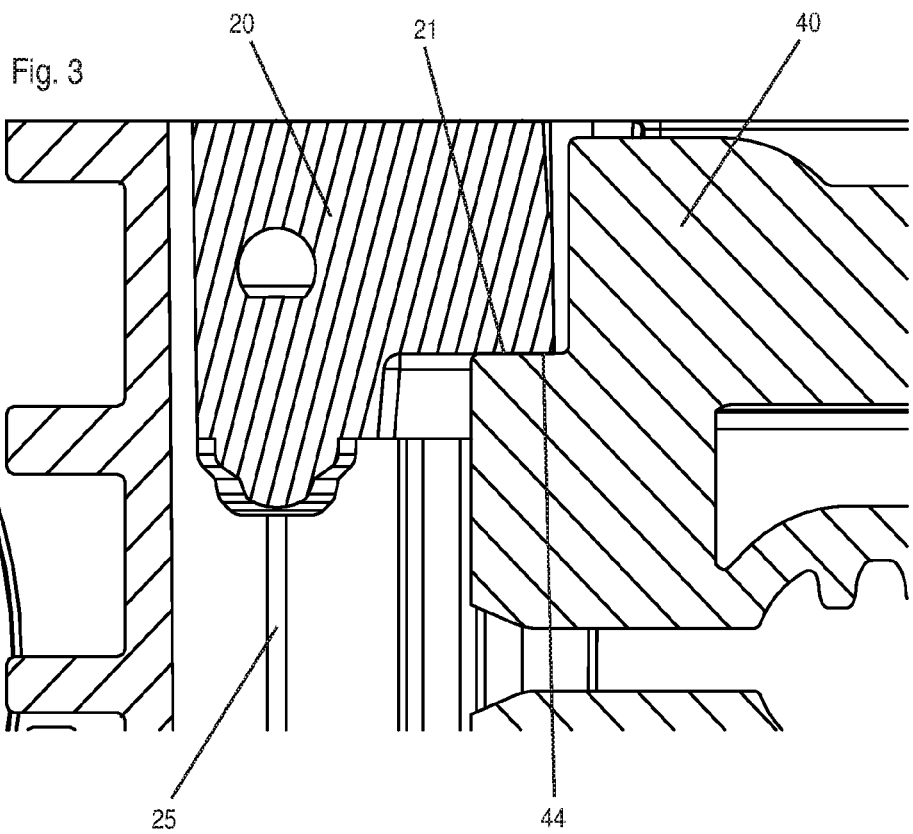
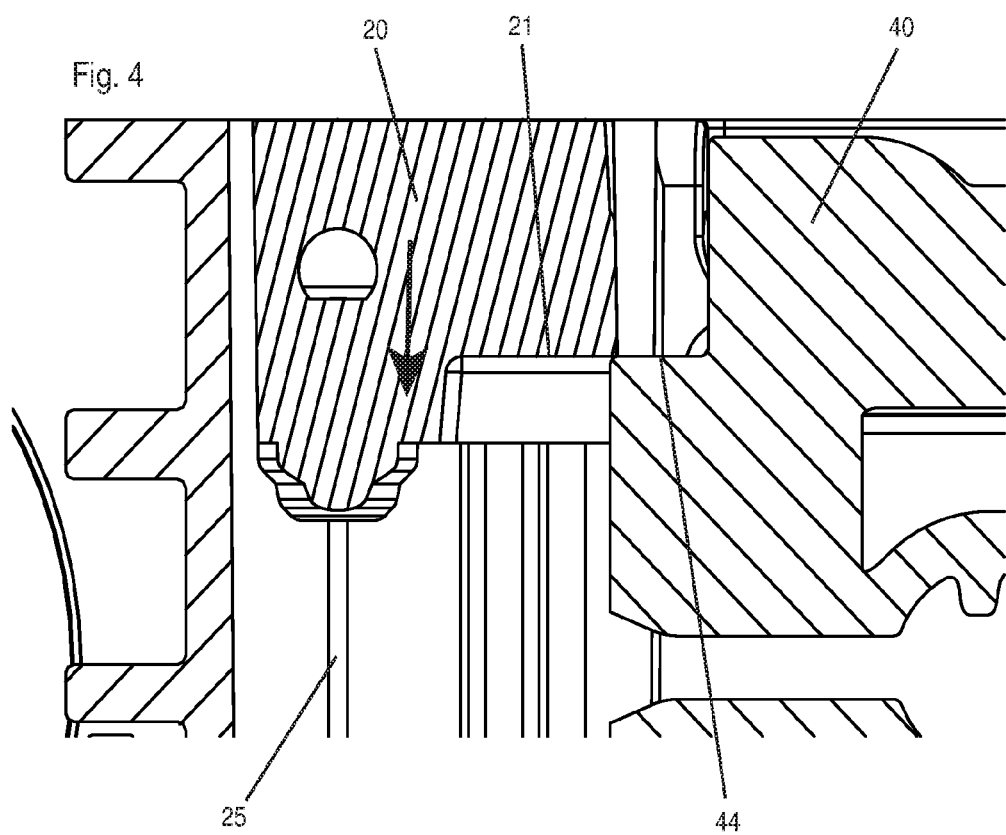

NEEDLE INSERTION AND RETRACTION MECHANISM

CROSS-REFERENCE TO RELATED APPLICATIONS

This application is a continuation of International Patent Application No. PCT/IB2019/055544, filed Jul. 1, 2019, entitled "NEEDLE INSERTION AND RETRACTION MECHANISM," which in turn claims priority to European Application No. 18186224.4, filed Jul. 30, 2018, entitled "NEEDLE INSERTION AND RETRACTION MECHANISM", each of which is incorporated by reference herein, in the entirety and for all purposes.

BACKGROUND

The present invention relates to a needle insertion and retraction mechanism for a medication delivery device for delivering a medicament. The medication delivery device may be an infusion device or an infusion pump. The medication delivery device may be a so-called patch pump, patch injector or bolus injector, that is adhered to the skin of the patient, for example, by virtue of an adhesive layer. The mechanism may have a needle insertion mechanism for insertion of a needle or a soft cannula into the skin of the patient for subcutaneous delivery of a medicament.

Devices for delivery of medication to the patient, which are particularly adhered to the skin of the patient, have been developed, either for delivery of multiple adjustable doses super-imposed on a basal rate (WO 02/40083 A2), or for multiple fixed doses including a basal rate (WO 2011/046950 A1). Those devices have been preliminarily developed for the treatment of diabetes, but also for the treatment of other diseases like cardio vascular diseases, auto-immune diseases or cancer for the delivery of a single dose as described in WO 2010/029054 A1, for example. Such a device is adhered to the patient's skin and activated automatically, or by the use of an activation button, or via a remote control system if the device is enabled to connect to other devices, and subsequently a single bolus volume will be injected.

The term "medicament" or "medication" includes any flowable medical formulation suitable for controlled administration through a means such as, for example, a cannula or a hollow needle and comprises a liquid, a solution, a gel or fine suspension containing one more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or delivered or analogous preparations), proteins and hormones, active ingredients derived from or harvested by biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriated basic, auxiliary and carrier substances.

A needle insertion and retraction mechanism for a medication delivery device is disclosed in WO 2017/219155 A1, for example.

SUMMARY

It is an object of the present invention to provide a needle insertion and retraction mechanism for a medication delivery device, which reliably provides for needle insertion and retraction, is cost effective and space-saving.

The object is addressed by the subject-matter of the claims, the description and the drawings.

The invention relates to a needle insertion and retraction mechanism, i.e., a mechanism which is adapted to automatically insert a needle and to automatically retract a needle. In an exemplary embodiment, a medication delivery device, particularly an infusion device or an infusion pump, may comprise the needle insertion and retraction mechanism disclosed herein. The medication delivery device may be formed as a patch pump, i.e., a medication delivery device which can be adhered to the skin of a human. The pump may be adhered to the skin by virtue of an adhesive layer provided on a surface of the housing of the medication delivery device.

More specifically, the medication delivery device may comprise at least a drive module and a needle insertion and retraction module. The drive module may have a drive motor and, for example, a controller for controlling the drive motor, a display, a battery casing and/or a battery to provide the energy for the drive motor, at least one control button, audible/visual indicators (e.g., LED lights). The drive module may comprise valuable components which are intended to be used multiple times.

The needle insertion and retraction module may have the needle insertion and retraction mechanism disclosed herein. The needle insertion and retraction module may be adapted to be attached to the drive module of the medication delivery device. Particularly the housing of the drive module is adapted to be attached to the housing of the needle insertion and retraction module, e.g., in a detachable form fit. In embodiments where the needle insertion and retraction module can be detached from the drive module, the drive module may be used multiple times, whereas the needle insertion and retraction module, which has been detached from the drive module, may be disposed and replaced by a new needle insertion and retraction module.

This may be the case when the product container, which can be a carpule, for example, is emptied. Expediently, the product container may be comprised by the needle insertion and retraction module. Therefore, the needle insertion and retraction module may comprise a product container holder adapted to retain a product container. If the product container is emptied, for example, the needle insertion and retraction module is detached from the drive module and replaced by a new one which comprises a new, i.e., filled, product container.

Particularly, the needle insertion and retraction module may be adapted to be attached to the drive module of the medication delivery device such that the motor of the drive module is or can be operatively connected or is operatively connectable to a control element of the needle insertion and retraction module to move it transversely with respect to the longitudinal axis of the needle from a starting position, via a needle insertion release position, to a needle retraction release position, as explained below. For example, the needle insertion and retraction module comprises a drive shaft which has a first coupling member and which is rotatable with respect to the housing of the needle insertion and retraction module. The drive shaft may be coupled with the control element such that rotation of the drive shaft in a first direction, particularly stepwise, results in linearly moving the control element, particularly stepwise, transversely with respect to the longitudinal axis of the needle from a starting position via, for example, a needle insertion release position to a needle retraction release position. The drive module may have a drive shaft which is coupled to the drive motor and which comprises a second coupling member which is adapted to be connected with the first coupling member to transmit rotational movement of the drive shaft of the drive module in rotational movement of the drive shaft of the needle insertion and retraction module. The drive module may be adapted such that a rotational movement of the motor in one direction is transmitted in a rotational movement of the drive shaft of the needle insertion and retraction module, whereas rotational movement of the motor in the opposite direction is not transmitted to the drive shaft of the needle insertion and retraction module. In exemplary embodiments, rotation of the motor in the opposite direction may be used to drive a piston rod mechanism to expel medicament from the product container.

The needle insertion and retraction mechanism for a medication delivery device for delivering a medicament may comprise a housing. The housing may be a single component housing or, expediently, a multi-component housing comprising two or more housing parts. Two or more housing parts may simplify assembly of the needle insertion and retraction mechanism and/or simplifies injection moulding of the housing parts. Furthermore, different materials can be used for different requirements of the different parts of the housing.

The needle insertion and retraction mechanism comprises a needle carrier, which holds a needle, i.e., a hollow needle. The needle is adapted to be inserted through the skin of a patient and to channel medication into the patient.

The needles may particularly remain in the patient while the medicament is channeled, for example, infused or injected, into the patient. In the alternative, embodiments are conceivable where a soft cannula, particularly a flexible tube, is inserted with inserting the needle and which remains in the patient, whereas the needle is retracted. In these alternative embodiments, medicament is channeled, for example, infused or injected, into the patient through the soft cannula while the needle is in its retracted position.

The needle is fixedly connected to the needle carrier, i.e., such that the needle cannot be detached from the needle carrier. Particularly movement of the needle carrier results in corresponding movement of the needle, and vice versa. The needle carrier can comprise a channel which is in fluid communication with the channel of the hollow needle.

The needle carrier may be linearly guided, particularly by the housing or another component of the needle insertion and retraction mechanism, to be moved along the longitudinal axis of the needle. For example, the housing forms a linear guide which linearly guides the needle carrier.

The needle insertion and retraction mechanism further comprises a first spring member and a second spring member. The first spring member is adapted to move the needle carrier with respect to the housing in a needle insertion direction along the longitudinal axis of the needle. The second spring member is adapted to retract the needle carrier with respect to the housing in a needle retraction direction, which is opposite to the needle insertion direction. The first spring member may be provided in a pre-tensioned state, and releasing the first spring member causes the first spring member to operate on the needle carrier to move the needle carrier in the needle insertion direction.

The second spring member may either be tensioned by moving the needle carrier in the needle insertion direction, or may be provided in a pre-tensioned state before the first spring member is released. If the second spring member is provided in a pre-tensioned state, the first spring member may advantageously be provided in smaller dimensions. On the other hand, tensioning the second spring member by moving the needle carrier in the needle insertion direction may be advantageous since it reduces the risk of creeping of the material which may be affected by a pre-tensioned spring.

In an exemplary embodiment, the first spring member is a spring which is separate from a spring which forms the second spring member. Therefore, first and second spring members may be formed by a separate spring, respectively. In another exemplary embodiment, the first and second spring members are commonly formed by a spring such that the first and second spring members are different sections of the same spring, respectively.

The first spring member may directly or indirectly operate on the needle carrier. Additionally or alternatively, the second spring member may operate directly or indirectly on the needle carrier. If the spring member acts directly on the needle carrier, it preferably contacts the needle carrier. In embodiments where the spring member indirectly operates on the needle carrier, one or more intermediate members can be provided between the needle carrier and the spring member.

The needle insertion and retraction mechanism further comprises a control element. The control element is intended or adapted to control the release of the first spring member to move the needle carrier in the longitudinal direction and the release of the second spring member to move the needle carrier in the needle retraction direction, for example. The control element is linearly movable, preferably guided by, for example, the housing, with respect to the housing to be moved transversely, particularly perpendicularly, with respect to the longitudinal axis of the needle, i.e., transversely with respect to the needle insertion direction and/or the needle retraction direction. For this purpose, the housing may form a linear guide. The control element may be moved, particularly stepwise, from a starting position via, for example, a needle insertion release position to a needle retraction release position. Preferably, the control element is moved from the starting position to the needle insertion release position, and from the needle insertion release position to the needle retraction release position, in a first direction with respect to the housing, respectively. In other words, the control element is linearly moved in one direction only from the starting position to the needle insertion release position and then to a needle retraction release position. In some embodiments the control element can additionally be moved in the first direction into or via a spike insertion release position.

The control element may be operatively coupled to the needle carrier, for example, it may engage the needle carrier, to prevent the needle carrier from being moved in the needle insertion direction, when the control element is in its starting position. In the starting position the pre-tensioned first spring member is operatively coupled to the needle carrier. Additionally or alternatively, the second spring member is decoupled from the needle carrier. If the second spring member is decoupled from the needle carrier, when the control element is in its starting position, the second spring member may be provided in a pre-tensioned state. In the alternative, the second spring may be coupled to the needle carrier when the control element is in its starting position, particularly in embodiments where the movement of the needle carrier in the needle insertion direction causes the second spring member to be tensioned.

When the control element is in its needle insertion release position, the control element is decoupled from the needle carrier, for example, it disengages the needle carrier, such that the first spring member drives the needle carrier including the needle, in the needle insertion direction into a needle insertion position. In other words, when the control element is moved from the starting position in the first direction to the needle insertion release position, the control element is decoupled from the needle carrier when the control element reaches the needle insertion release position. Since the first spring member, indirectly or directly, operates on the needle carrier it drives the needle carrier in the needle insertion direction until the needle carrier abuts a stop when the needle insertion position is reached. Particularly, the first spring member may retain the needle carrier in the needle insertion position, for example, until retraction is triggered or the control element is moved in the needle retraction release position. The first spring member drives the needle carrier from a position, in which the needle is completely within the housing, i.e., the needle tip does not protrude from the outer surface of the housing, into the needle insertion position, in which the needle protrudes from the outer surface of the housing, i.e., the needle tip protrudes by a distance from the housing corresponding to the desired insertion depth.

When the control element is in its needle retraction release position, the second spring member is operatively coupled to the needle carrier such that the second spring member drives the needle carrier in the needle retraction direction. In other words, in the needle retraction release position the second spring member operates on the needle carrier, directly or indirectly, such that the spring member drives the needle carrier in the needle retraction direction, which is opposed to the needle insertion direction. Particularly, by moving the control element from the needle insertion release position to the needle retraction release position, the second spring member is released such that it drives the needle carrier in the needle retraction direction. In preferred embodiments, the first spring member is decoupled from the needle carrier, when the control element is in its retraction release position. Furthermore, the second spring member is coupled to the needle carrier to drive it in the needle retraction direction. In alternative embodiments, the first spring member may remain coupled to the needle carrier when the pre-tensioned second spring member is released such that the pre-tensioned second spring member both drives the needle carrier in the needle retraction direction and tensions the first spring member. In this embodiment, the mechanism which causes the needle carrier to be retracted can be less complex, since only the second spring member is to be operatively coupled to the needle carrier and the first spring member does not need to be decoupled from the needle carrier.

In some embodiments, the needle insertion and retraction mechanism may include a first intermediate member arranged between the first spring member and the needle carrier and/or a second intermediate member arranged between the second spring member and the needle carrier. Advantages of an intermediate member may be at least one of reducing friction, enhancing reliability of the mechanism and reducing the requirement for small tolerances regarding the dimension of the spring member.

The first intermediate member may be linearly guided by the control element in the needle insertion direction. The control element may form a linear guide to guide the first intermediate member linearly. The first intermediate member may be connected to the control element such that it is linearly guided in the needle insertion direction. Because the first intermediate member is linearly guided by the control element, it is movable together with the control element when the control element is moved from the starting position in the first direction or via the needle insertion release position to the needle retraction release position. Hence, the first intermediate member is linearly movable with respect to the control element in the needle insertion direction and is movable together with the control element transversely with respect to the needle insertion direction.

The first intermediate member or the first spring member directly may be engaged with the needle carrier, when the control element is in its starting position. Furthermore, the needle carrier may be engaged with the control element, when the control element is in its starting position, whereby movement of the needle carrier in the needle insertion direction is prevented. The control member is adapted to be disengaged from the needle carrier by moving the control element transversely with respect to the needle insertion direction, i.e., in the first direction. By disengaging the control element from the needle carrier, the first spring member may operate in one embodiment directly on the needle carrier or in anther embodiment on the first intermediate member and the first intermediate member may operate on the needle carrier. Hence, the first spring member drives the first intermediate member and the needle carrier in the needle insertion direction. The first spring member drives the first intermediate member and the needle carrier until one of the needle carrier or the first intermediate member abuts a stop when the needle carrier is in the needle insertion position.

The first intermediate member or the first spring member is adapted to be disengaged from the needle carrier by moving the control element, particularly together with the first intermediate member transversely with respect to the needle insertion direction. By disengaging the first intermediate member or the first spring member from the needle carrier, the needle carrier is free to be moved in the needle retraction direction. Particularly the second spring may drive the needle carrier together with the needle in the needle retraction direction, provided the needle carrier is not otherwise prevented from being moved in the needle retraction direction. In embodiments where the first spring member directly operates on the needle carrier, the first intermediate member may be unnecessary, for example, depending on the configuration of the first spring member or a component thereof (e.g., the configuration of an arm of the first spring member or requirements for tight tolerances of the dimensions of the first spring member).

The second intermediate member may be linearly guided by the control element in the needle retraction direction whereby the second intermediate member is linearly movable with respect to the control element in the needle retraction direction. The control element may form a linear guide for linearly guiding the second intermediate member in the needle retraction direction. The linear guide preferably prevents the second intermediate member from being moved with respect to the control element in the direction in which the control element is linearly guided. Therefore, the second intermediate member is movable together with the control element transversely with respect to the needle retraction direction.

The second intermediate member or the second spring member may be adapted to be engaged with the housing when the control element is in its starting position and/or in its insertion release position. Thereby, the second spring member can be retained in a pre-tensioned state, or pre-vented from being released. When the second intermediate member or the second spring member is engaged with the housing, it may be disengaged from the needle carrier. The second intermediate member or the second spring member may be adapted to be disengaged from the housing and engaged with the needle carrier by moving the control element from its needle insertion release position transversely with respect to the needle retraction direction, particularly by moving the control element together with the second intermediate member in the first direction or particularly from the insertion release position to the needle retraction position. By disengaging the second intermediate member or the second spring member from the housing and engaging it with the needle carrier the second spring member is able to drive and drives the second intermediate member and the needle carrier in the needle retraction direction. The second spring member, in one embodiment, directly operates on the needle carrier, and in another embodiment, operates on the second intermediate member and the second intermediate member operates on the needle carrier in the needle retraction direction. In embodiments where the second spring member directly operates on the needle carrier, the second intermediate member may be unnecessary, for instance, depending on the configuration of the second spring member or a component thereof (e.g., the configuration of an arm of the second spring member or requirements for tight tolerances of the dimensions of the first spring member).

By moving the needle carrier in the needle retraction direction into a needle retraction position, the needle is completely retracted or moved into the housing, i.e., such that the needle tip does not protrude from the outer surface of the housing.

In preferred embodiments, the first spring member comprises a spring arm and the first intermediate member or the needle carrier has a convexly curved contact surface on which the spring arm rests and particularly slides and/or rolls over when the first spring member drives the needle carrier or the first intermediate member together with the needle carrier into the needle insertion position. Because of the convexly curved contact surface the cooperation between the spring arm and the needle carrier or the first intermediate member can be optimized with respect to friction. The convexly curved contact surface effects that the spring arm slides and/or rolls over when the spring arm of the spring member drives the needle carrier or the first intermediate member together with the needle carrier in the needle insertion direction.

Additionally or alternatively, the second spring member may comprise a spring arm and the second intermediate member or the needle carrier may have a convexly curved contact surface on which the spring arm of the second spring member rests, and particularly slides and/or rolls over when the second spring member drives the needle carrier or the second intermediate member together with the needle carrier into the needle retraction position. Because of the convexly curved contact surface the cooperation between the spring arm and the needle carrier or the second intermediate member can be optimized with respect to friction. The convexly curved contact surface effects that the spring arm slides and/or rolls over when the spring arm of the second spring member drives the needle carrier or the second intermediate member together with the needle carrier in the needle retraction direction.

The first spring member and/or the second spring member, for example, may respectively be one of helical spring, a leaf spring, a compression spring, a pull spring, a torsion spring, a leg spring, a spiral spring, a Belleville spring (e.g., disc spring), or a combination thereof.

In preferred embodiments, the first spring member may comprise a first spring arm and the second spring member may comprise a second spring arm. The first spring arm operates directly or indirectly on the needle carrier. The first spring member may comprise a first resilient spring section which is adapted to store the spring energy for driving the needle carrier in the needle insertion direction. The second spring arm may operate directly or indirectly on the needle carrier. The second spring member may comprise a second resilient spring section for storing the spring energy to drive the needle carrier in the needle retraction direction.

The first resilient spring section may be a torsion spring section, particularly a helical spring section which is torsionally loaded. The second resilient spring section may be a torsion spring member, particularly a helical spring section which is torsionally loaded.

The first torsion spring section may be supported on the control element or the housing. The second torsion spring section may be supported on the control element or the housing. Particularly, the first spring member and/or the second spring member are at least rotationally supported on the control member, such that pivoting the arm of the respective spring member strains, i.e., tensions the spring, particularly the resilient spring section or the helical spring section.

The first spring member and/or the second spring member may be located on the control element, such that the respective spring member is movable together with the control element. Particularly the first spring member and/or the second spring member may be embedded in the control element, or the first and/or second spring members may partly surround a section of the control element. Preferably, the helical section of the spring member surrounds a section, particularly a cylindrical section, of the control element. The section of the control element may extend through the helical spring section.

In exemplary embodiments, the first spring member may be supported on the control element, for instance, the first resilient spring section is located between where the first spring member is supported on the control element and where the first spring member, particularly the arm of the first spring member, operates directly or indirectly on the needle carrier. As a result, energy can be stored in the first resilient spring section by pivoting the arm, and releasing energy stored in the first resilient spring section pivots the arm in the opposite direction to drive the needle carrier in the needle insertion direction.

Additionally or alternatively, the second spring member may be supported on the control element and the second resilient spring section may be located between where the second spring member is supported on the control element, and the second spring member, particularly the arm of the second spring member, operates directly or indirectly on the needle carrier. As a result, energy can be stored in the second resilient spring section by pivoting the arm, and releasing energy stored in the second resilient spring section pivots the arm in the opposite direction to drive the needle carrier in the needle retraction direction.

Particularly, the first spring member may comprise a first arm which protrudes from the first resilient section and directly or indirectly operates on the needle carrier. For example, the first arm is supported on the needle carrier or the first intermediate member. Additionally or alternatively, the second spring member may comprise a second arm which protrudes from the second resilient section and directly or indirectly operates on the needle carrier. For example, the second arm is supported on the needle carrier or on the second intermediate member.

In some embodiments, the first spring member and the second spring member are integrally formed by one spring. This means that one spring provides the functionality of the first spring member and the second spring member. The first resilient spring section and the second resilient spring section may be interconnected by an interconnecting section of the spring. Preferably the interconnecting section of the spring provides the support for the first and second spring members on the control element. The interconnecting section may be fixedly supported on the control element or at least supported such that rotation of the interconnecting section with respect to the control element about an axis about the first and second arms can be pivoted is prevented. Generally preferred is that the torsion spring section or the first and/or second resilient spring sections may be tensioned about an axis which extends transversally with respect to the longitudinal axis of the needle or the needle insertion or retraction directions.

The spring or the first and second spring members may be made from a suitable material, e.g., a metal material, such as spring steel, alternatively plastic material or a hybrid between a plastic material and a metal. For example, the spring may be a metal spring coated with plastic material.

In the needle insertion and retraction mechanism, the first and second spring members each may be formed by a separate spring, or may be integrally formed by one spring. Preferably, the first spring member and the second spring member each comprise a resilient spring section, which may be selected from a torsion spring section or a helical spring section. In case a helical spring section is selected, then this section preferably surrounds a section of the control element.

In the needle insertion and retraction mechanism, the first spring member may be supported on the control element and a first resilient spring section may be located between where the first spring member is supported on the control element and where the first spring member operates on the needle carrier, and/or the second spring member is supported on the control element and a second resilient spring section is located between where the second spring member is supported on the control element and where the second spring member operates on the needle carrier. Preferably, the first spring member comprises a first arm which protrudes from the first resilient section and operates on the needle carrier, for example is supported directly on the needle carrier or via a first intermediate member. The second spring member preferably comprises a second arm which protrudes from the second resilient section and operates directly on the needle carrier, for example, is supported on the needle carrier or via the second intermediate member.

In the needle insertion and retraction mechanism, the first spring member and the second spring member may be integrally formed by one spring, where the first resilient spring section and the second resilient spring section are interconnected by an interconnecting section of the spring, and where the interconnecting section provides the support for the first and second spring members on the control element. Preferably, the interconnecting section comprises a torsional or helical spring section.

In a further aspect, the needle insertion and retraction mechanism may comprise a spike carrier, which holds or forms a hollow spike. The spike is intended to pierce a wall of a product container. The spike carrier is linearly guided, particularly by the housing, to be moved from a first position to a second position. In the first position the hollow spike does not pierce the wall of the container, whereas in the second position, the spike has pierced the wall of the product container. The spike may be arranged such that it axially aligns with the pierceable wall of the product container. The wall, particularly a septum or a stopper, of the product container may be made from an elastomer material such as rubber. The product container may be comprised by the needle insertion and retraction module, which comprises the needle insertion and retraction mechanism. For example, the needle insertion and retraction module comprises a retainer or (cartridge) holder adapted to retain and/or affix the product container. The retainer or holder may be a part of or formed by the housing.

The hollow spike may be formed by or comprise a hollow needle. For example, the spike may comprise a hollow body and a hollow needle, such as a transfer cannula, which is connected to the hollow body, particularly by material fit, such as bonding. The needle may be partially inserted in and fit to the hollow body, and the needle may protrude from the hollow body, such that, for example, the needle can pierce the wall of the product container.

The hollow spike is adapted to pierce the wall of the product container when the spike is being moved from the first position to the second position. Particularly, the tip of the spike is formed such that it can easily penetrate through the wall. The housing may comprise a linear guide which engages the spike carrier such that the spike carrier is movable from the first position to the second position. The hollow spike comprises a channel through which the medicament can be expelled from the container.

The hollow spike and the needle are in fluid communication, preferably by a flexible tube, particularly comprising a lumen, which interconnects the hollow spike and the needle. For example, at one end of the flexible tube the lumen may either directly end into the channel of the needle, or into a channel of the needle carrier that connects the lumen with the channel of the needle. At the other end of the flexible tube, the lumen may either directly end into the channel of the spike, or into a channel of the spike carrier that connects the lumen with the channel of the spike. An advantage when the lumen directly ends into the channel of the needle and/or the spike is that there is less contact between the medicament and different materials that may contain leachable components that can diffuse from the plastic into the medicament.

When the spike carrier is in its first position the needle is not in fluid communication with the medication. When the spike carrier is in its second position the needle is in fluid communication with the medication. This allows the spike and/or the medicament to be kept sterile. Furthermore, this allows for the fluid communication between the needle and the medicament to be established immediately before medication should be administered.

For example, the spike and/or the spike carrier can be moved in the second position before, during or after the needle and/or the needle carrier are moved in the needle insertion direction. Particularly, in a first step the needle and/or the needle carrier are moved into the needle insertion position. In a second step, for example, carried out after the first step, the spike and/or the spike carrier are moved into the second position. Alternatively, the second step can be carried out before the first step. However, in this alternative, there may be a risk that medication leaks out from the product container while the needle has not yet been inserted in the body resulting in drop formation at the needle tip. Otherwise, in this alternative, priming of the fluid system may be easily performed.

Basically, the spike carrier can be moved from the first position to the second position by, for example, a motor; one or more springs; one or more resilient parts; a drive such as a hydraulic drive, a pneumatic drive, an electromagnetic drive, or a shape memory alloy driven drive, etc. In preferred embodiments, the needle insertion and retraction mechanism or module comprises a spike insertion spring, which operates on the spike carrier to drive the spike carrier from the first position to the second position. For example, the spike insertion spring can be supported on the housing and the spike carrier. The spring may be a leaf spring or a helical spring. The helical spring may be a conical helical spring or a cylindrical helical spring. A conical helical spring may be advantageous for space saving, since it can take up a flat shape when it is compressed.

In some embodiments, the control element prevents the spike carrier from being moved from the first position to the second position. For example, the control element may engage the spike carrier mechanically such that movement of the spike carrier from the first position to the second position is prevented. By moving the control element, particularly in the first direction, the spike carrier may be released to be moved from the first position to the second position. For example, the control element is disengaged from the spike carrier by movement of the control element. Particularly, the control element is released or disengaged from the spike carrier when the control element is moved from its starting position to a spike insertion release position. In the spike insertion release position, the control element releases or is disengaged from the spike carrier. When the spike carrier is released, the at least one of aforesaid drives, particularly the spring or pre-tensioned spring, drives the spike carrier from the first position to the second position, thereby piercing the wall, particularly the septum, of the product container.

The control element may be moved from the starting position in the first direction via the spike insertion release position, the needle insertion release position to the needle retraction release position. Particularly, the control element may be moved to the spike insertion release position and from the spike insertion release position to the needle insertion release position.

The effect is that the spike is moved in the second direction before the needle carrier is moved in the needle insertion direction to insert the needle. This could be advantageous since a priming step can be conducted. During the priming step a small amount of medicament is expelled from the product container to remove air from the fluid guiding parts including the spike, the flexible tube and the needle, before the needle carrier is moved in the needle insertion direction, i.e., the needle is inserted. This prevents air from being administered into the patient.

In the alternative, the control element can be moved in the needle insertion release position and from the needle insertion release position to the spike insertion release position. This effects that the needle is inserted before the spike pierces the wall of the product container. It is further conceivable that the spike insertion release position and the needle insertion release position coincide. As a result, the needle carrier and the spike carrier are moved in the needle insertion position or the second position at the same time.

Preferably, the longitudinal axis of the spike is transverse, particularly perpendicular, and offset with respect to the longitudinal axis of the needle. Therefore, the direction in which the spike carrier is guided is transverse, particularly perpendicular, to the direction in which the needle carrier is guided. This allows the mechanism to be compact, since a longitudinal product container, such as a carpule, is preferably arranged in parallel to the surface which is adhered to the skin of the patient. It is generally preferred that the needle is perpendicular to the skin of the patient or the surface from which it protrudes if it is inserted.

The needle insertion and retraction mechanism or module may comprise a drive shaft which is rotatably guided by the housing. The rotational axis of the rotational shaft can be arranged in parallel to the longitudinal axis of the spike and/or transverse, particularly perpendicular to the longitudinal axis of the needle. The rotational axis of the drive shaft may be offset from the longitudinal axis of the needle and/or from the longitudinal axis of the spike. The drive shaft is operatively connected to the control element such that rotation of the drive shaft in a first rotational direction causes the control element to be moved in a first longitudinal or linear direction from the starting position to at least one of the spike insertion release position, the needle insertion release position and the needle retraction release position. Preferably the drive shaft is driven gradually in the first rotational direction to move the control element gradually, i.e., stepwise, to the aforesaid positions.

The drive shaft may comprise a gear wheel, e.g., a pinion or round gear, which engages a gear rack formed by the control element. Thereby, rotation of the drive shaft is converted in a linear or longitudinal movement of the control element.

Furthermore, the drive shaft may comprise a coupling member adapted to be coupled with a coupling member of a drive shaft of a drive mechanism.

BRIEF DESCRIPTION OF THE DRAWINGS

The invention has been described by way of a plurality of embodiments, aspects and examples. In the following, one embodiment of the invention is described with reference to the enclosed drawings.

FIG. 3 illustrates a control element which is engaged with the needle carrier.

FIG. 4 illustrates the control element disengaging the needle carrier.

DETAILED DESCRIPTION

Figure 1:
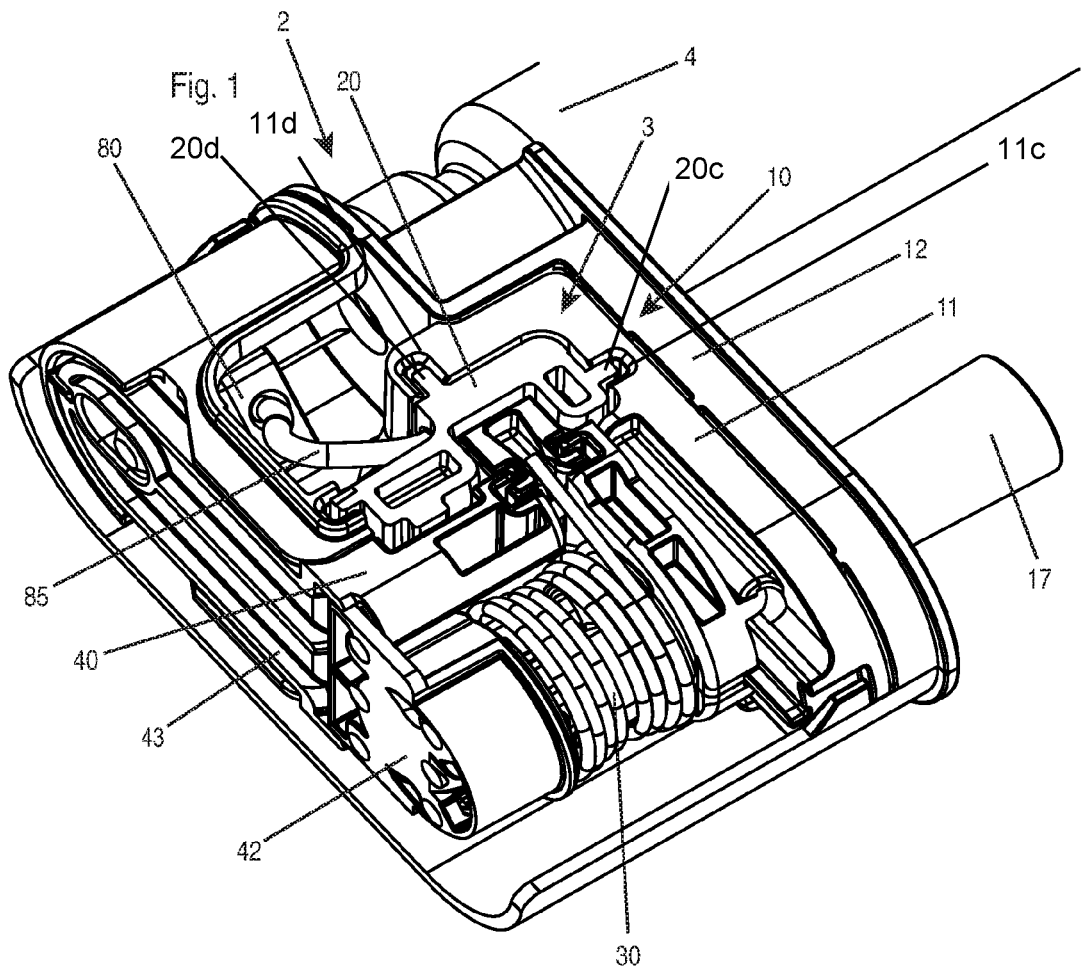
FIG. 1 illustrates a perspective view of a needle insertion and retraction module including a needle insertion and retraction mechanism according to embodiments of the present disclosure.

Referring to FIGS. 1 to 19, an embodiment of a needle insertion and retraction module 2 including a needle insertion and retraction mechanism 3 is disclosed. As can be seen in FIG. 1 the needle insertion and retraction mechanism 3 comprises a housing 10 which is a multiple component housing. Particularly, the housing 10 comprises a first housing 11 and a second housing 12 which are connected to each other by positive fit or by firmly bonding or welding. Alternatively, the first and the second housings 11, 12 are molded as a single part.

Figure 2:
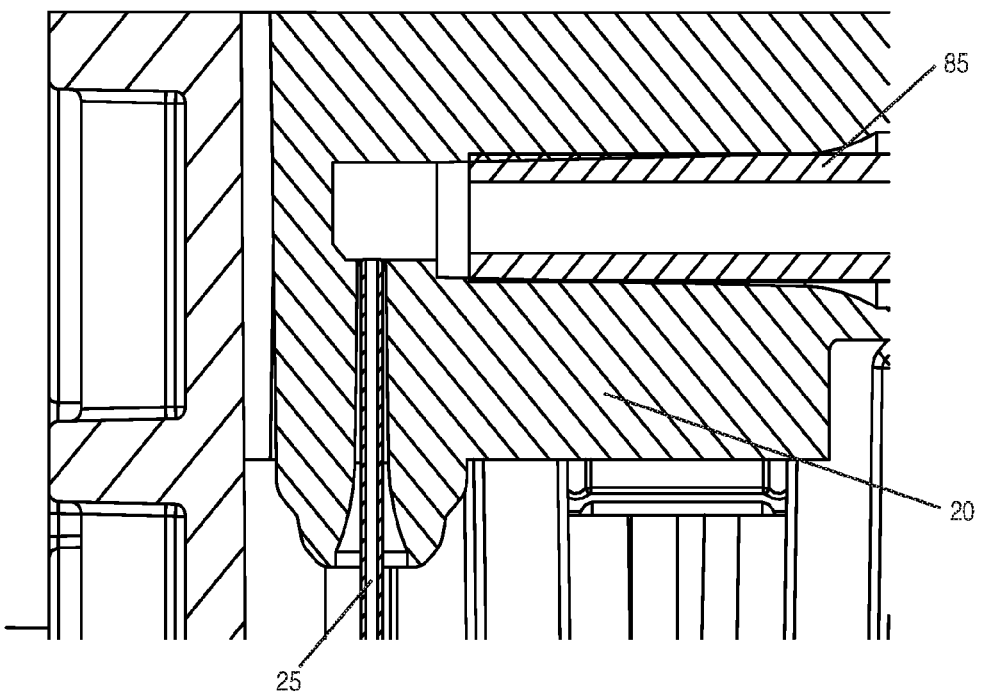
FIG. 2 illustrates a cross-sectional view through a needle carrier of the needle insertion and retraction mechanism.

The needle insertion and retraction mechanism 3 comprises a needle carrier 20 which holds a needle 25 (FIG. 2) and which is linearly guided by the housing 10, particularly by the first housing 11. The housing 10 or the first housing 11 comprises a longitudinal guide (FIG. 1) which engages the needle carrier 20 such that it is movable along the longitudinal axis of the needle 25. The longitudinal guide comprises at least a first longitudinal groove 11c and a second longitudinal groove 11d formed by the housing 11. The needle carrier 20 comprises at least a first rib 20c and a second rib 20d where the first rib engages the first groove and the second rib engages the second groove. Thereby the needle carrier 20 is linearly guided to be moved along the longitudinal axis of the needle 25. The needle carrier 20 is movable between an initial position (FIG. 1) in which the needle 25 which protrudes from the needle carrier 20 in a needle insertion direction is completely encompassed by the housing, and a needle insertion position (FIGS. 6 and 7) in which the needle 25 protrudes from an outer surface of the housing 10, particularly the surface which is intended to be contacted or adhered to the skin of a patient. The housing 10 may comprise an opening or a pierceable wall through which the needle 25 is moved when the needle carrier 20 is moved from its initial position to its needle insertion position. The longitudinal axis of the needle 25 is substantially perpendicular or normal with respect to the surface which is intended to be adhered to the skin of the patient. The needle 25 is a hollow needle through which a medication or a medicament can be injected into the patient. The housing 10, particularly the housing 12 is adapted to retain a product container 4. In the example shown, the product container 4 is a carpule, with a pierceable septum 5 (wall) (FIG. 9) at its forward end. The medicament of the product container 4 can be expelled through a flexible tube 85, which is in fluid communication with the hollow needle 25, such that the medicament travels through the needle 25 into a patient. As can be seen in FIG. 2 the needle carrier 20 comprises a channel which connects an end of the flexible tube 85 and the hollow needle 25 in a fluid guiding manner. The needle 25 is fixedly retained in a bore of the needle carrier 20. The flexible tube 85 is with one end fixedly retained in a bore of the needle carrier 20.

The other end of the flexible tube 85 is fixedly retained in a bore of a spike carrier 80 which connects a hollow spike 70 in a fluid guiding manner with the flexible tube 85 (FIG. 1), by means of a channel formed by the spike carrier 80. The spike 70 is fixedly retained in a bore of the spike carrier 80. One end of the flexible tube 85 is fixedly retained in a bore of the spike carrier 80.

The needle insertion and retraction mechanism 3 further comprises a first spring member 31 (FIG. 5) which is adapted to move the needle carrier 20 with respect to the housing 10 in a needle insertion direction along the longitudinal axis of the needle 25. Furthermore, a second spring member 32 (FIG. 13) is provided which is adapted to retract the needle carrier 20 with respect to the housing 10 in a needle retraction direction, which is opposed to the needle insertion direction. In the embodiment shown, the first spring member 31 and the second spring member 32 are integrally formed by one spring 30. However, in an alternative, spring members 31 and 32 can be separate from one another.

Figure 8:
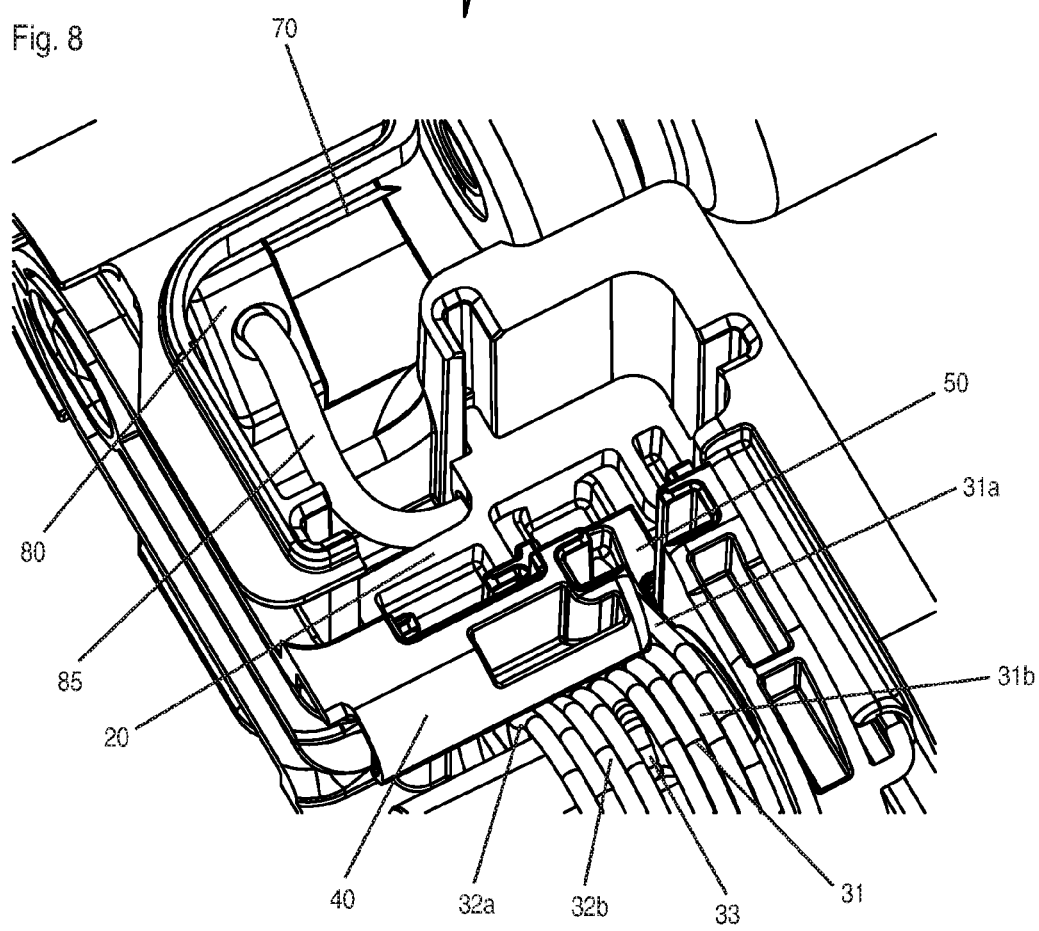
FIG. 8 illustrates a spike carrier with a spike in a first position.

The first spring member 31 comprises a first helical spring section 31b which operates as a torsion spring (FIG. 8). A first arm 31a protrudes from the circumference of the first helical spring section 31b. The first spring member 31 is supported on a control element 40 such that the first helical spring section 31b can be strained or tensioned by pivoting the arm 31a. Furthermore, the energy stored in the first helical spring section 31b can be released whereby the first arm 31a is pivoted in a direction which causes the needle carrier 20 to move in the needle insertion direction.

The second spring member 32 comprises a second helical spring section 32b which operates as a torsion spring. A second arm 32a protrudes from circumference of the second helical spring section 32b. The second spring member 32 is supported on the control element 40 such that the second helical spring section 32b can be strained or tensioned by pivoting the arm 32a. Furthermore, the energy stored in the second helical spring section 32b can be released whereby the second arm 32a is pivoted.

The first helical spring section 31b and the second helical spring section 32b surround a portion of the control element 40. This portion comprises a slit which retains an interconnecting section 33 of the spring 30 which interconnects the first helical spring section 31b and the second helical spring section 32b and which also provides the support section of the first spring member 31 and the second spring member 32 for straining or tensioning the spring sections 31a and 31b. In embodiments with two separate spring members 31 and 32 each of them can comprise a supporting section by which the spring member 31, 32 is supported on the control element 40.

Figure 18:
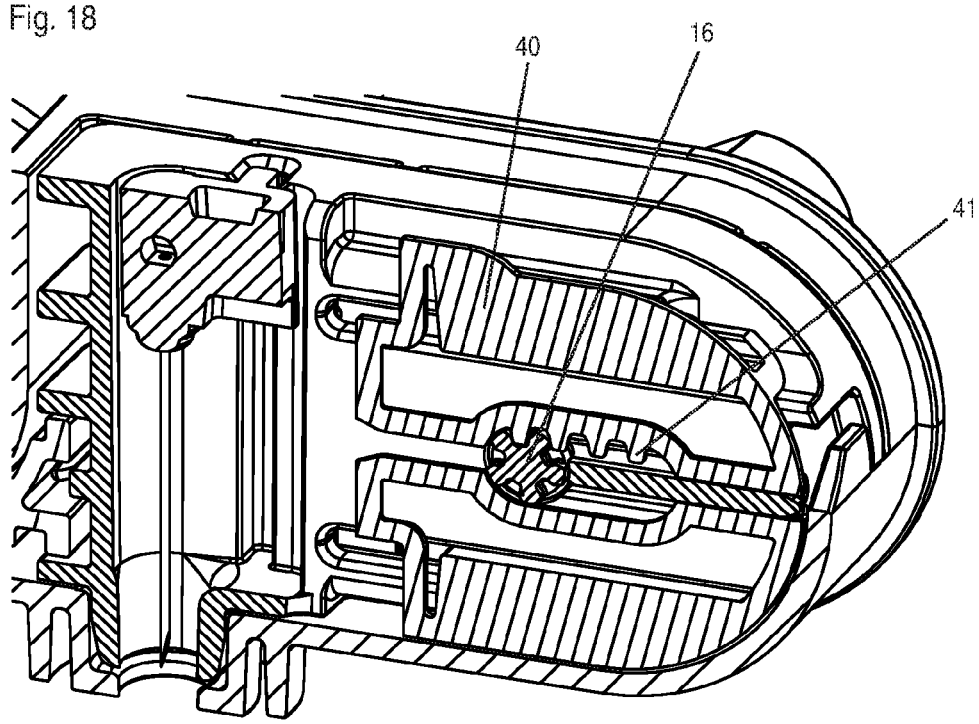
FIG. 18 illustrates the control element which has been moved in its needle retraction position.
Figure 19:
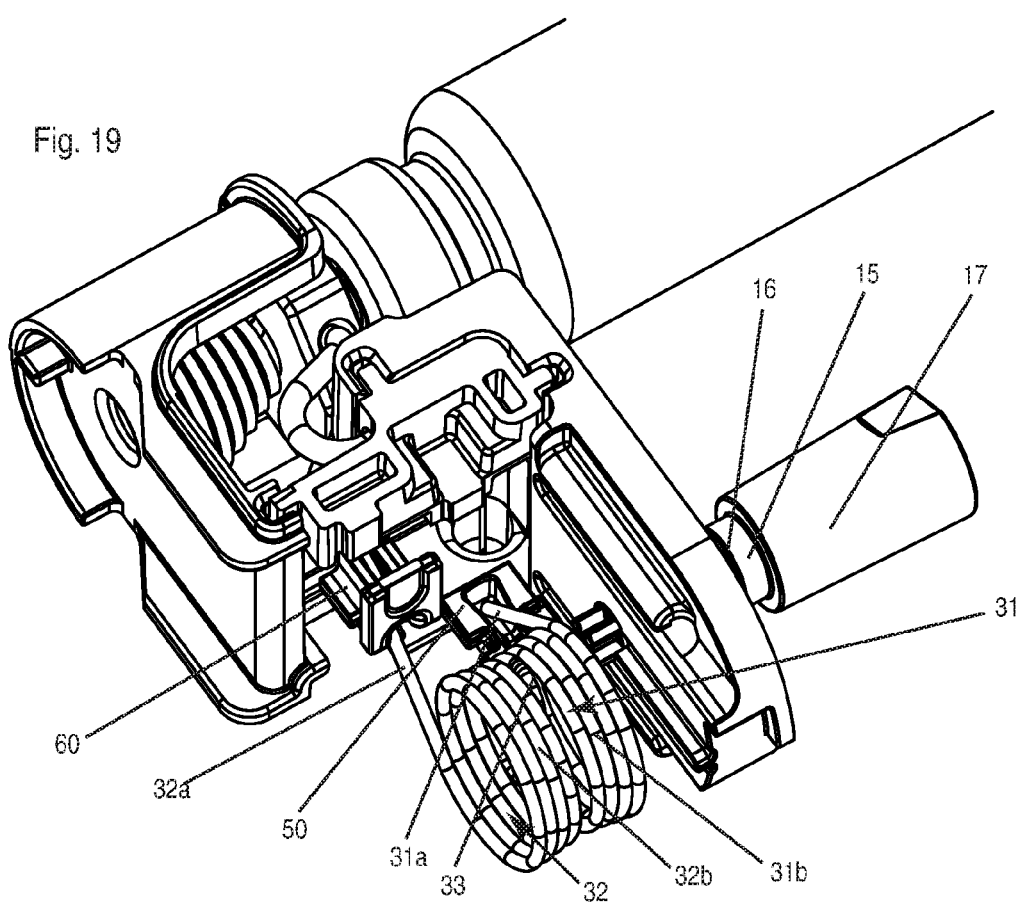
FIG. 19 illustrates a spring for moving the needle carrier in the needle insertion direction and in the needle retraction direction.

A control element 40 is linearly guided with respect to the housing 10 to be moved transversely with respect to the longitudinal axis of the needle 25. The control element 40 can be moved from a starting position (FIG. 16) via a needle insertion release position (FIG. 17) to a needle retraction release position (FIG. 18). The control element 40 moves from the starting position to the needle retraction release position, including the positions between the starting position and the needle retraction release position, in the same direction. The spring 30 or the spring members 31, 32 are attached to the control element 40 such that they move together with the control element 40. The needle insertion and retraction mechanism 3 or module 2 provides for a drive shaft 15 which is rotatably guided by the housing 10, e.g., by virtue of a rotational bearing (FIG. 19). The drive shaft 15 is operatively connected to the control element 40. The drive shaft 15 and the control element 40 are adapted to cooperate with each other such that rotation of the drive shaft 15 in a first rotational direction causes the control element 40 to be linearly moved, namely transversely with respect to the longitudinal axis of the needle 25 because of the linear guidance provided by the housing 10.

The drive shaft 15 comprises a gear wheel 16 (FIGS. 16 to 18) which is formed by or connected to the drive shaft 15 and which engages a gear rack 41 formed by or connected to the control element 40. By rotating the drive shaft 15 or the gear wheel 16 the control element 40 is linearly moved.

The drive shaft 15 comprises a coupling member 17 which is adapted to be coupled with a coupling member of a drive shaft of a drive mechanism (not shown). Thereby, rotation of the drive shaft 15 of the drive mechanism in a first direction is transmitted to the drive shaft 15 in the first direction causing the control element 40 to be moved in the first longitudinal direction.

Figure 5:
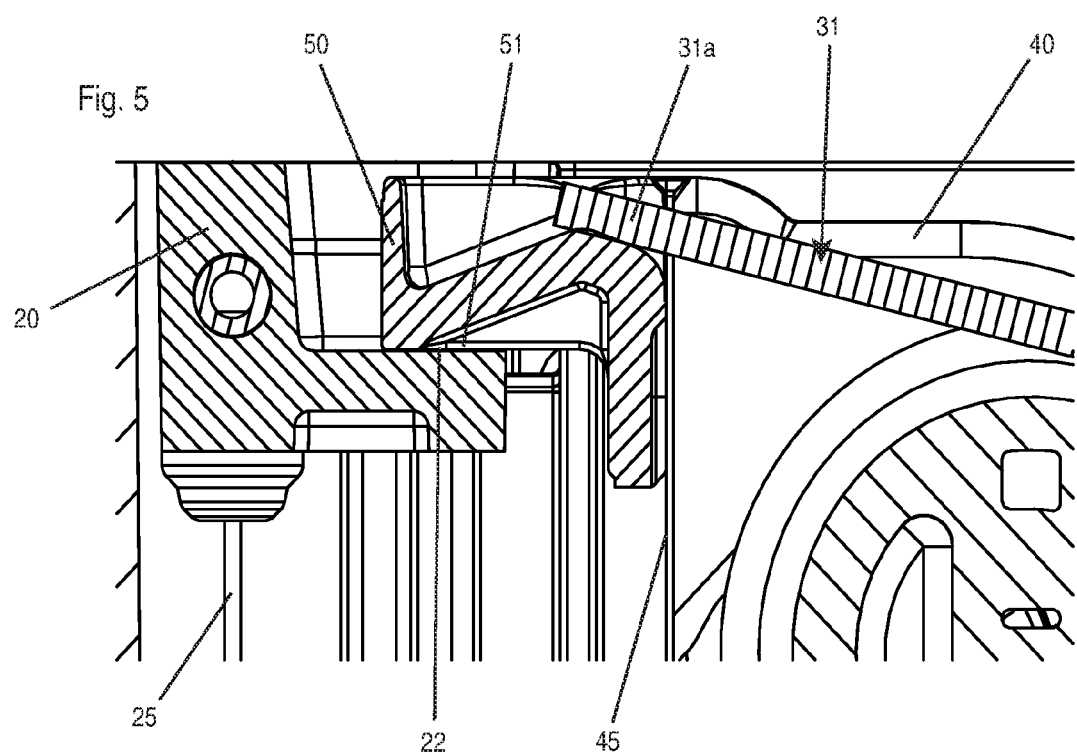
FIG. 5 illustrates a first intermediate member between a spring arm and a needle carrier with the needle carrier in a retracted position.
Figure 6:
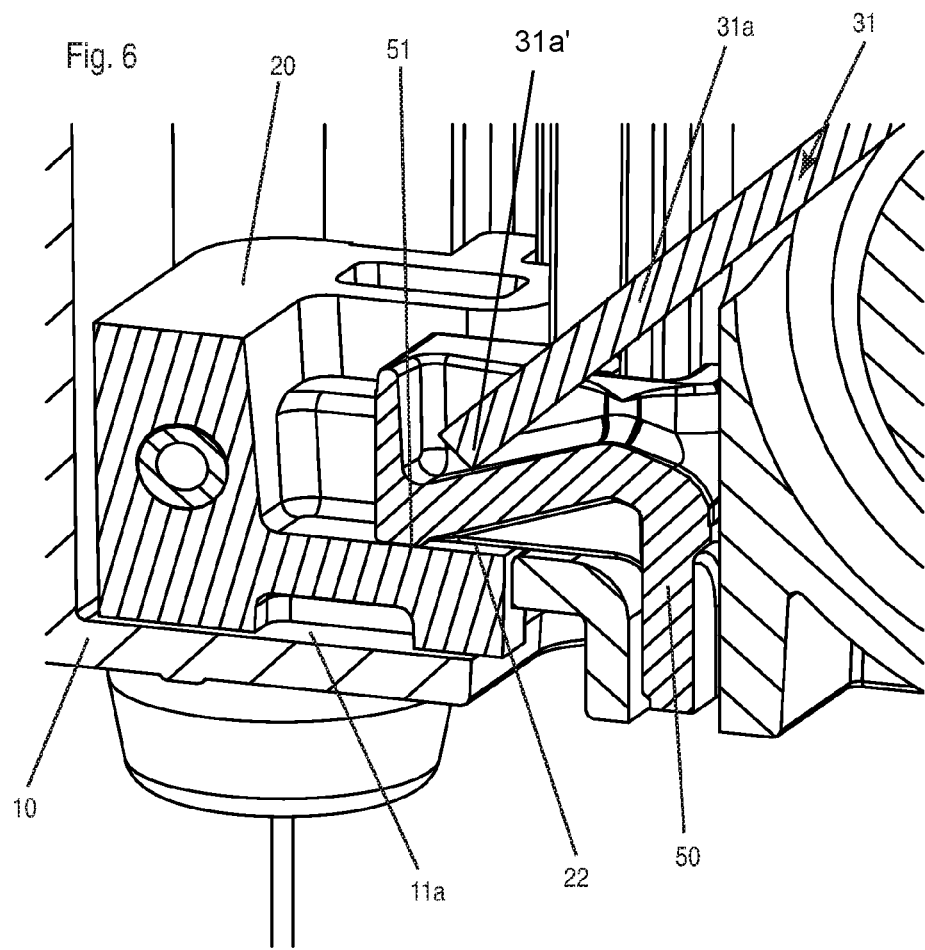
FIG. 6 illustrates the parts of FIG. 5 with the needle carrier in a needle insertion position.
Figure 7:
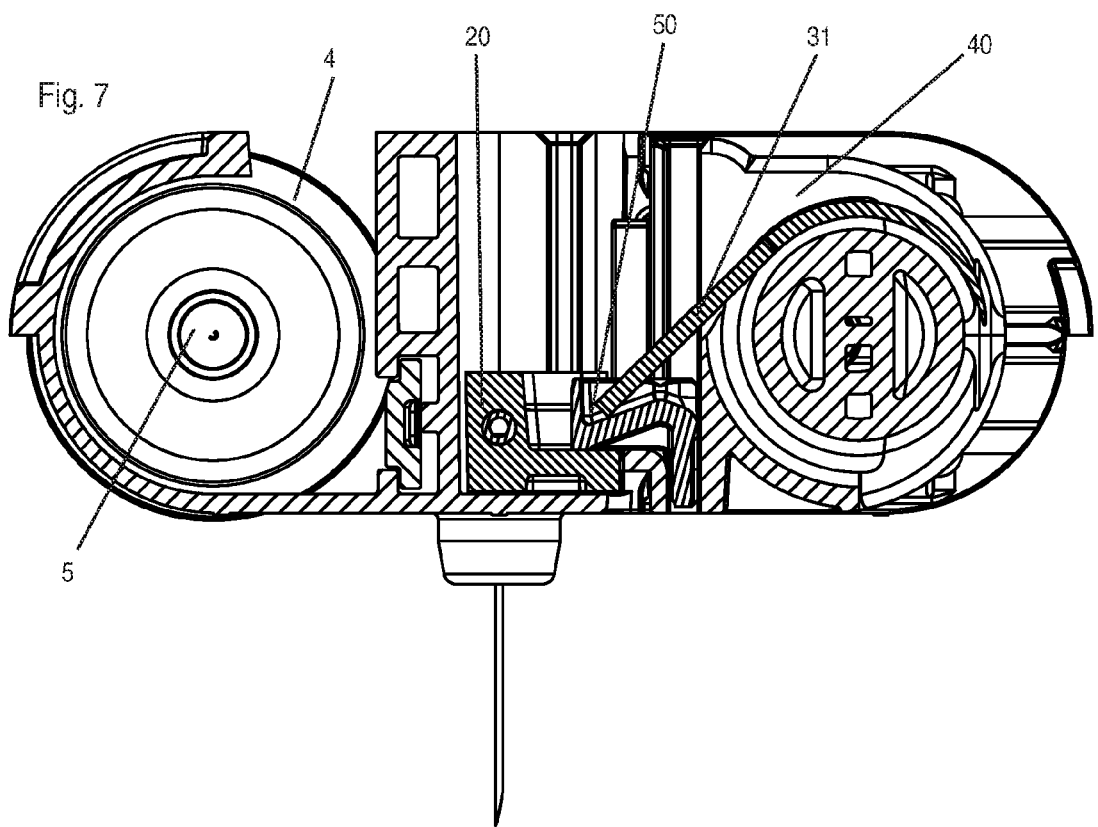
FIG. 7 illustrates a further view of the needle carrier in the needle insertion position.

The control element 40 comprises a cap 42 which is connected to a main body 43 of the control element 40 (FIG. 1). The cap 42 is connected to or partially fits over the portion which is surrounded by the helical spring sections 31b, 32b. The cap 42 keeps the spring 30 or the spring members 31, 32 in position on the control element 40 or the main body 43 (FIG. 1). The control element 40 is operatively coupled to the needle carrier 20 to prevent the needle carrier 20 from being moved in the needle insertion direction when the control element 40 is in its starting position (FIG. 3). As can be seen in FIG. 3, the control element 40 or its main body 43 comprises a stop surface 44 on which a counter stop surface 21 of the needle carrier 20 rests when the control element 40 is in its starting position. The needle carrier 20 is thereby prevented from being moved in the needle insertion direction. As can be seen in FIG. 4, the stop surface 44 disengages the counter stop surface 21 when the control element 40 is moved in its insertion release position such that the needle carrier 20 is free to be moved in the needle insertion direction. The first arm 31a or more generally the spring member 31 operates on the needle carrier 20 via a first intermediate member 50 (FIG. 5) to drive the needle carrier 20 from the initial position (FIG. 5) in the needle insertion direction into a needle insertion position (FIG. 6).

A first intermediate member 50 comprises a counter stop surface 51 which engages a stop surface 22 of the needle carrier 20 when the control element 40 is in its starting position and/or in its insertion release position. The first spring member 31 applies a spring force on the first intermediate member 50 which in turn transmits the spring force to the needle carrier 20 as long as the first intermediate member 50 and the needle carrier 20 are in engagement. A spring powered movement of the needle carrier 20 in the needle insertion direction, when the control element 40 is in its starting position, is prevented when stop surface 44 and counter stop surface 21 are engaged (FIG. 3). As soon as the control element 40 and the needle carrier 20 are disengaged, the first spring member 31 drives the needle carrier 20 in the needle insertion direction until the needle carrier 20 abuts an axial stop 11a (FIG. 6) provided by the housing 10, particularly by the first housing 11, in the needle insertion position of the needle carrier 20. The control element 40 comprises a linear guide 45 (FIG. 12) which is adapted to linearly guide the first intermediate member 50 in the direction of the longitudinal axis of the needle 25 or the needle insertion and retraction direction (FIG. 5). The linear guide 45 causes the first intermediate member 50 to be moved together with the control element 40 transversely with respect to the longitudinal axis of the needle from the starting position via at least the needle insertion release position to the needle retraction release position. By moving the control element 40 from its starting position to its needle insertion release position, the first intermediate member 50 is moved with respect to the needle carrier 20 but does not yet disengage from the needle carrier 20. That is to say that the first intermediate member 50 and the needle carrier 20 remain engaged in the needle insertion release position of the control element 40.

Figure 12:
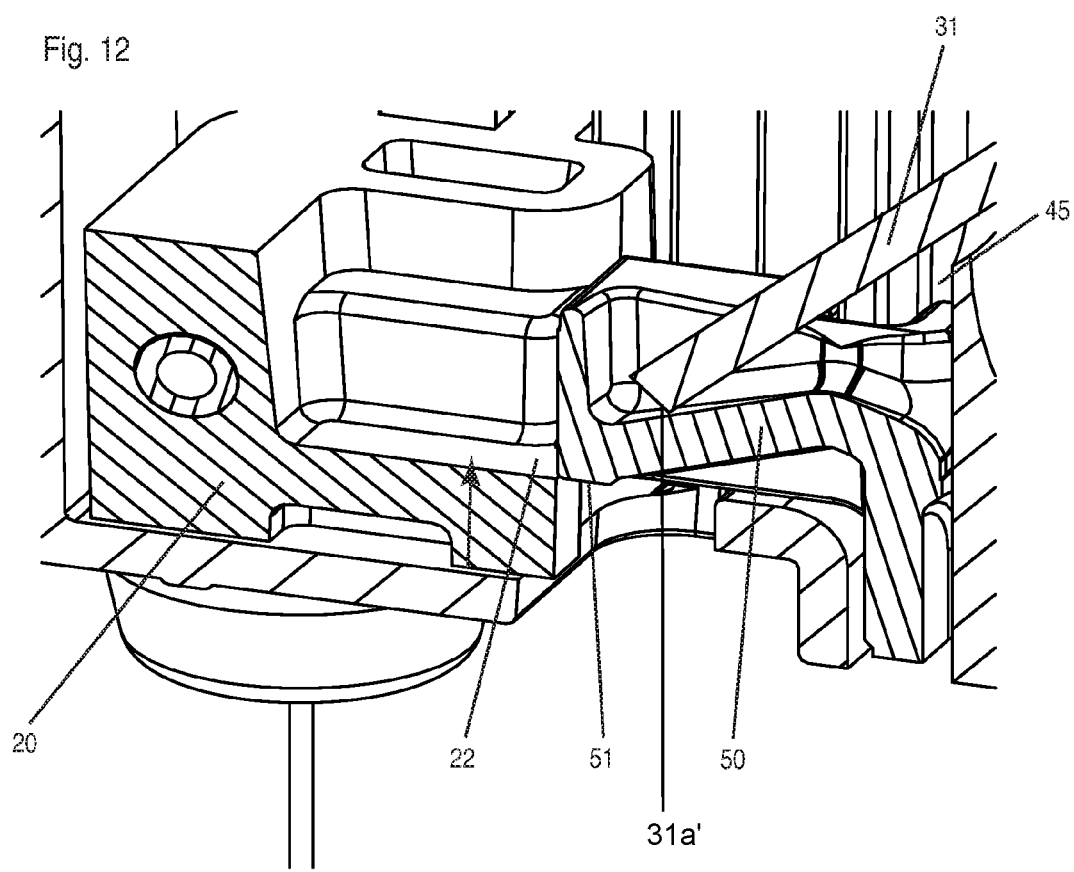
FIG. 12 illustrates the first intermediate member disengaged from the needle carrier.

When the control element 40 is further moved in the first direction to its retraction release position, the second spring member 32 is operatively coupled to the needle carrier 20 such that the second spring member 32 drives the needle carrier 20 in the needle retraction direction. By moving the control member 40 into the needle retraction release position the first intermediate member 50 and the needle carrier 20, particularly the stop surface 22 and the counter stop surface 51, disengage since the first intermediate member 50 is moved together with the control element 40 transversely with respect to the longitudinal axis of the needle 25. The needle carrier 20 is now free to be moved in the needle retraction direction which is opposed to the needle insertion direction (FIG. 12).

For example, when the first intermediate member 50 is disengaged from the needle carrier 20, and being driven by the remainder of the spring force of the first spring member 31, the first intermediate member 50 abuts a stop formed by the control element 40, particularly by the end of the linear guide 45. Thereby, the remainder of the spring force of the first spring member 31 is advantageously prevented from interfering with the further operation of the mechanism.

A second intermediate member 60 (FIG. 13) is provided, which is linearly guided by the control element 40 in the needle retraction direction, e.g., by a linear guide 46 provided by the control element 40. The linear guide 46 is adapted such that the second intermediate member 60 is linearly movable with respect to the control element 40 along the longitudinal axis of the needle 25 or in the needle retraction direction. Furthermore, the linear guide 46 causes the second intermediate member 60 to be moved together with the control element 40 transversely with respect to the needle retraction direction or transversely with respect to the longitudinal axis of the needle 25.

Figure 13:
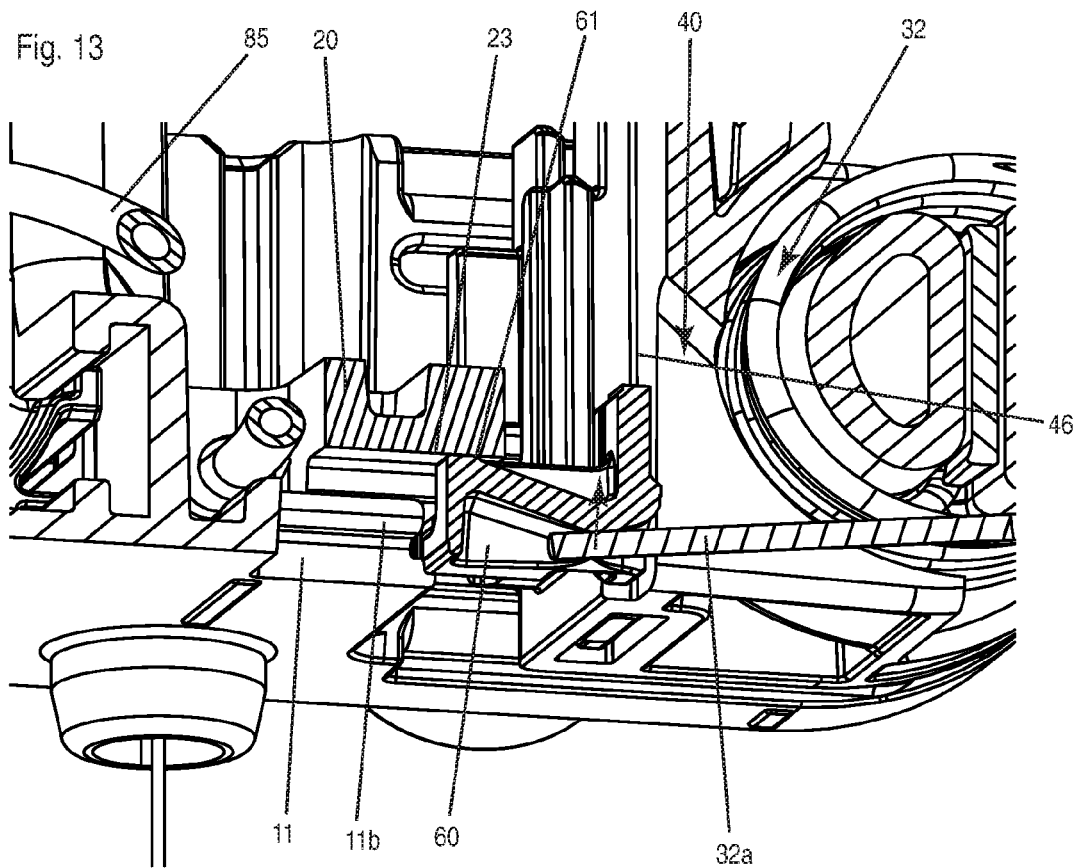
FIG. 13 illustrates a second intermediate member between a second spring arm and the needle carrier, in which the intermediate member is disengaged from the housing and engaged with the needle carrier.
Figure 14:
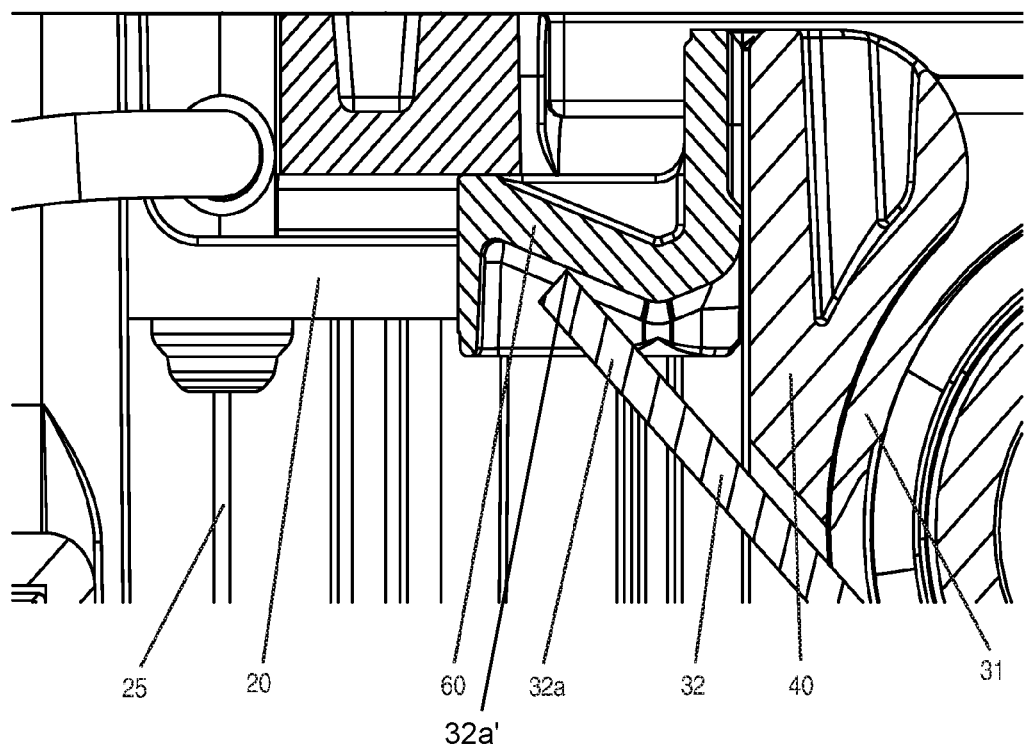
FIG. 14 illustrates the needle carrier which has been moved in the retracted position.
Figure 15:
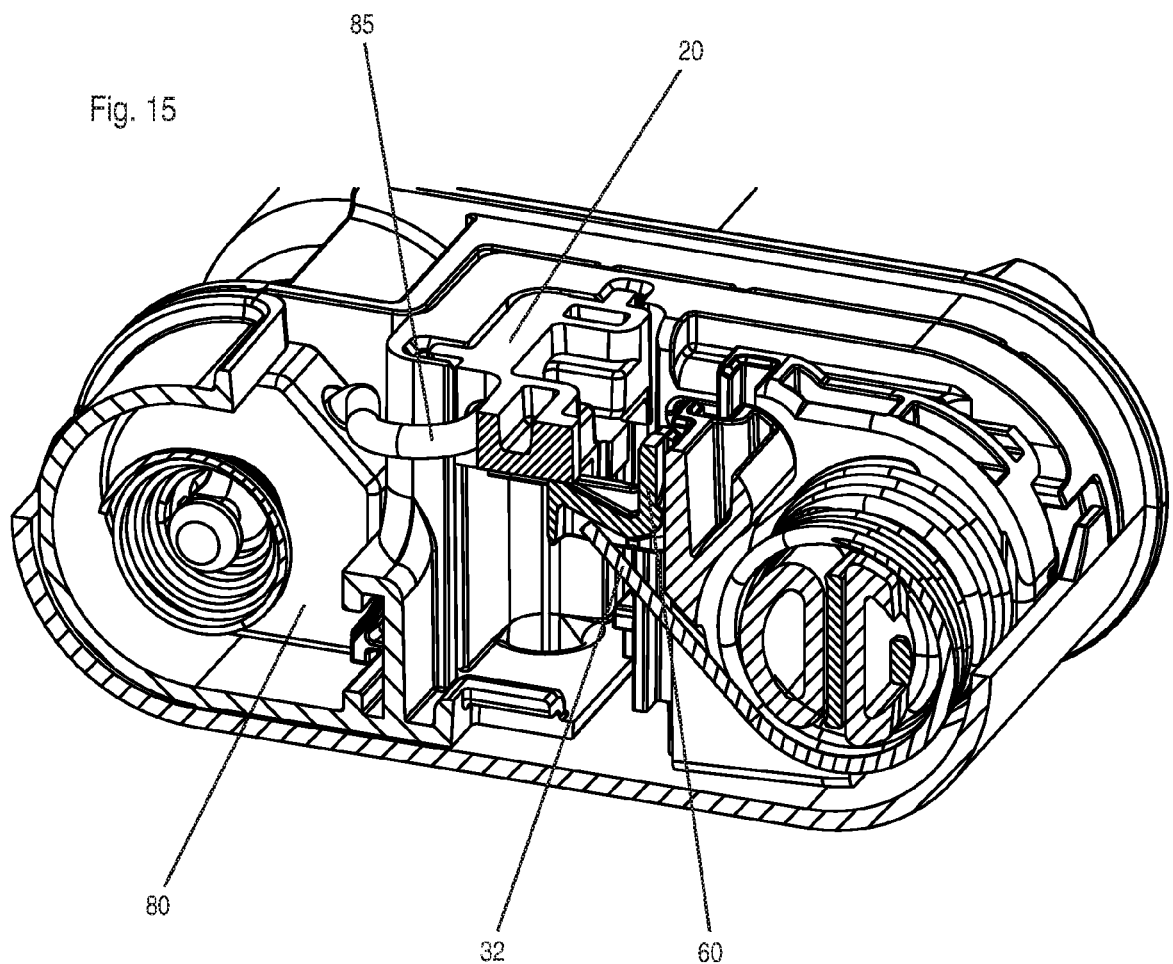
FIG. 15 illustrates a perspective view of the needle carrier which has been moved in the retracted position.
Figure 16:
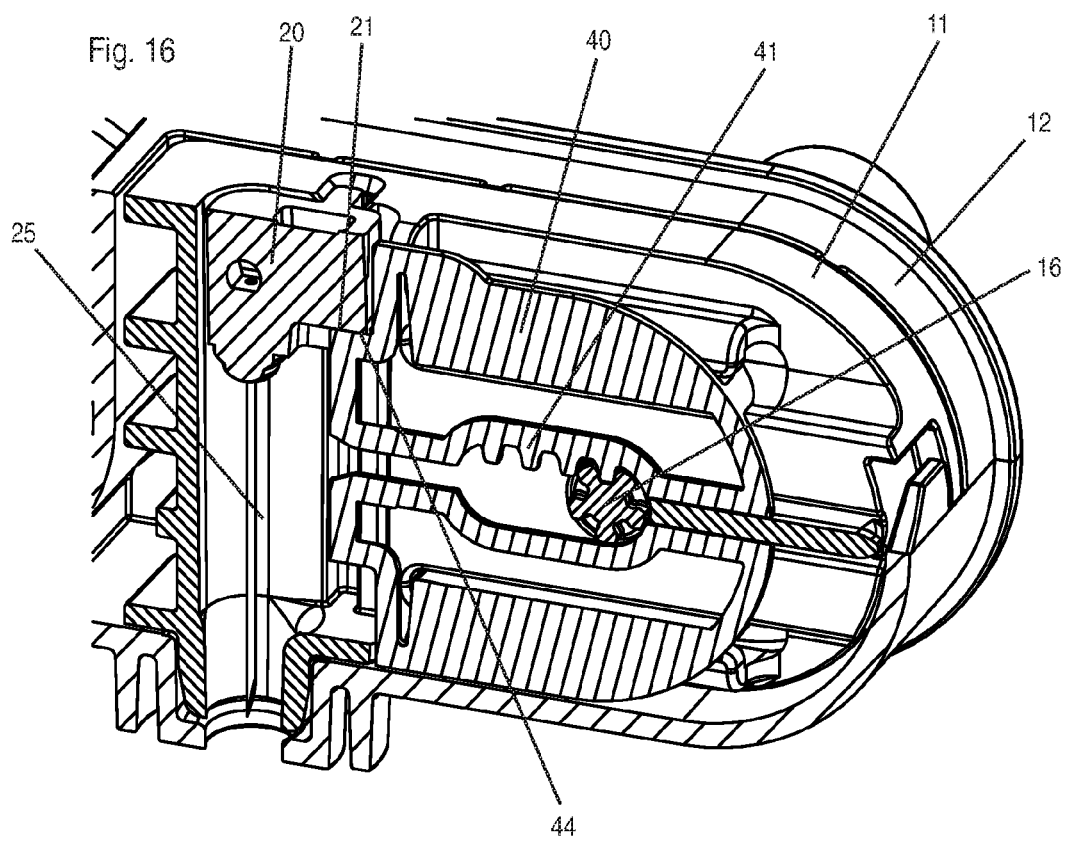
FIG. 16 illustrates a control element in its starting position.
Figure 17:
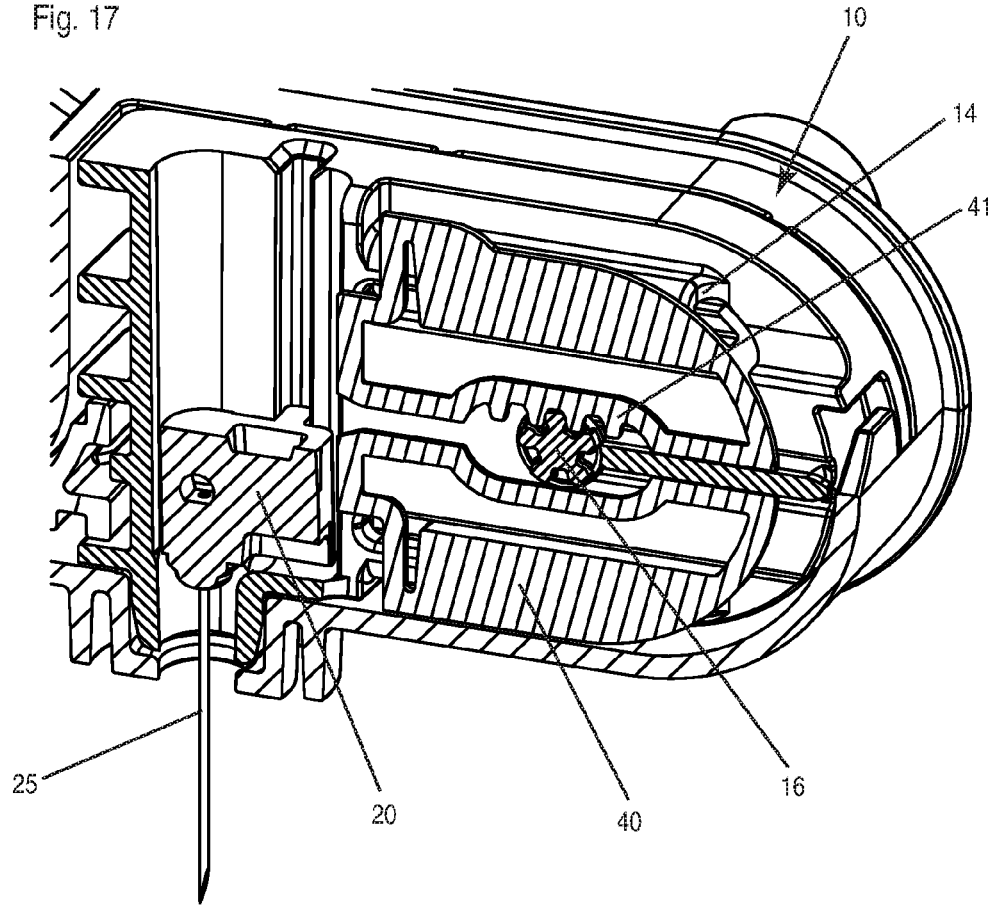
FIG. 17 illustrates a control element which has been moved in the needle release position.

When the control element 40 is in its starting position and/or in its insertion release position, the second intermediate member 60 is engaged with the housing 10, particularly the housing 11, such that the second intermediate member 60 is prevented from being moved in the needle retraction direction (FIG. 13). The housing 10 comprises a stop surface 11b with which the second intermediate member 60 is engaged to prevent the second intermediate member 60 from being moved in the needle retraction direction. The second spring member 32 applies a spring force on the second intermediate member 60 in the needle retraction direction. By moving the control element 40 into its retraction release position the second intermediate member 60 is disengaged from the housing 10, particularly from the stop surface 11b. Furthermore, the second intermediate member 60 or a counter stop surface 61 thereof engages with the needle carrier 20 or a stop surface 23 thereof. Thereby, the second intermediate member 60 and the needle carrier 20 are moved in the needle retraction direction driven by the second spring member 32 (FIG. 13). Thereby the needle carrier 20 is moved in its retracted position such that the needle 25 is completely retracted into the housing 10 (FIGS. 14 and 15).

To prevent the first intermediate member 50 and the second intermediate member 60 from interfering with each other, they are positioned axially offset from one another particularly in the direction which is transversal with respect to the longitudinal axis of the needle 25 (FIG. 19). Preferably, the first intermediate member 50 and the second intermediate member 60 are offset from each other in the direction of the longitudinal axis of a needle spike 70.

The first spring arm 31a rests on a convexly curved contact surface of the first intermediate member 50 as can be seen in FIG. 5. During a state when the first intermediate member 50 is driven by the first spring member 31 in the needle insertion direction, the spring arm 31a, particularly its circumference surface, moves over the apex of the convexly curved contact surface, thereby the first arm 31a (or its circumference surface) particularly slides and/or rolls over the convexly curved contact surface. This arrangement reduces friction and/or reduces the risk of malfunction with respect to other arrangements.

Movement of the needle carrier 20 in the needle retraction direction is prevented at least by the remainder of the spring force of the first spring member 31 operating on the first intermediate member 50, as long as the first intermediate member 50 is engaged with the needle carrier 20 (FIG. 6).

Furthermore, as shown in FIG. 6, the free end of the first spring arm 31a comprises an edge 31a', for example, formed between the circumference surface and the end face of the first spring arm 31a. When the needle carrier 20 is in its needle insertion position, the edge 31a' contacts or rests on and even to a small or microscopic extent, grooves into, the first intermediate member 50, e.g., on an inclined surface thereof. The edge 31a' contacting or even grooving into the first intermediate member 50 increases friction between the first intermediate member 50 and the first spring arm 31a. Thereby, movement of the needle carrier 20 in the needle retraction direction is, in addition to the remainder of the spring force of the first spring member 31, made more difficult or even prevented as long as the first intermediate member 50 is engaged with the needle carrier 20. The angle between the inclined surface and the circumference surface may, for example, be smaller than the angle between the end face and the circumference surface.

The second spring arm 32a rests on a convexly curved contact surface of the second intermediate member 60 as can be seen in FIGS. 13 and 14. While the second intermediate member 60 is driven by the second spring member 32 in the needle retraction direction, the spring arm 32a moves over the apex of the convexly curved contact surface, thereby the second arm 32a particularly slides and/or rolls over the convexly curved contact surface. This arrangement reduces friction and/or reduces the risk of malfunction with respect to other arrangements.

Movement of the needle carrier 20 back in the needle insertion direction is prevented at least by the remainder of the spring force of the second spring member 32 operating on the second intermediate member 60 as long as the second intermediate member 60 is engaged with the needle carrier 20 (FIG. 14).

Furthermore, as shown in FIG. 14, the free end of the second spring arm 32a comprises an edge 32a', for example, formed between the circumference surface and the end face of the second spring arm 32a. When the needle carrier 20 is in its needle retraction position, the edge 32a' contacts or rests on, and even to a small or microscopic extent, grooves into, the second intermediate member 60, e.g., on an inclined surface thereof. The edge 32a' contacting or even grooving into the second intermediate member 60 increases friction between the second intermediate member 60 and the second spring arm 32a. Thereby, movement of the needle carrier 20 back in the needle insertion direction is, in addition to the remainder of the spring force of the second spring member 32, made more difficult or even prevented as long as the second intermediate member 60 is engaged with the needle carrier 20. The angle between the inclined surface and the circumference surface may, for example, be smaller than the angle between the end face and the circumference surface.

Figure 9:
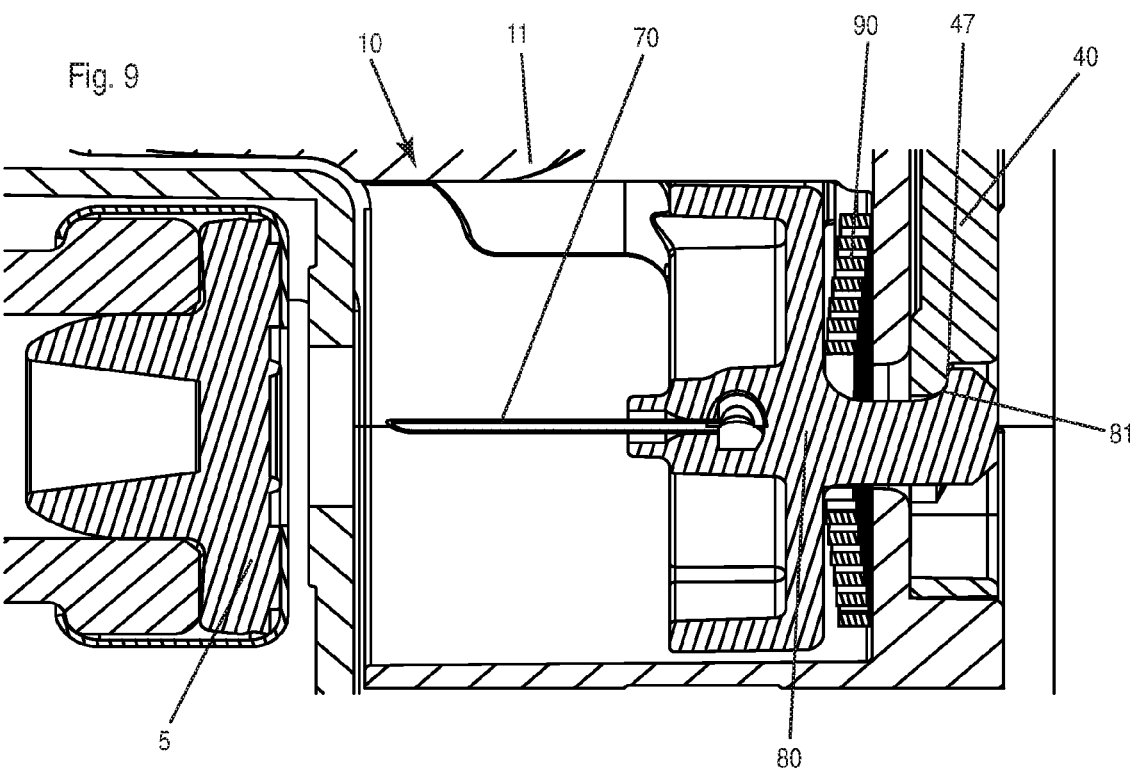
FIG. 9 illustrates a cross-sectional view of the spike carrier in a first position.
Figure 10:
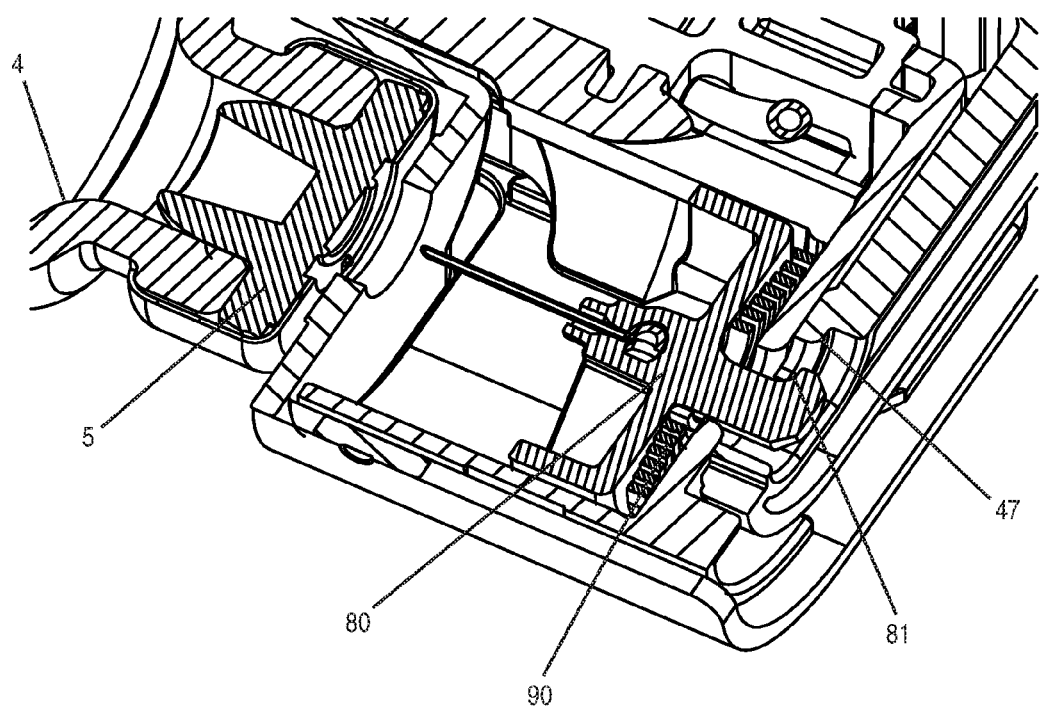
FIG. 10 illustrates a cross-sectional view of the spike carrier being released to be moved in a second position.

The spike carrier 80 holds a hollow spike 70 which protrudes from the spike carrier 80 to a receptacle for the product container or to a pierceable wall of the product container, when the product container is inserted in the receptacle (FIGS. 8 to 11). In FIGS. 9 and 10 the spike carrier 80 is in a first position in which the spike 70 does not pierce the wall 5 of the product container 4. The spike carrier 80 is linearly guided, e.g., by a linear guide provided by the housing 10, preferably by the housing 11, such that the spike carrier 80 can be moved linearly from a first position to a second position together with the spike 70. By moving the spike carrier 80 from the first position to the second position the spike 70 pierces the septum 5 of the product container 4 such that the spike 70 establishes a fluid communication between the medication inside the product container 4 and the needle 25. A spring 90 is provided, which operates on the spike carrier 80 to drive the spike carrier 80 from the first position to the second position. In the first position of the spike carrier 80, the spring 90 is in a pre-tensioned condition. A variety of spring designs may be conceivable, whereby a conical helical spring 90 is preferred. One end of the spring 90 is supported on the spike carrier 80 and the other end of the spring 90 is supported on the housing 10, particularly the housing 11.

Figure 11:
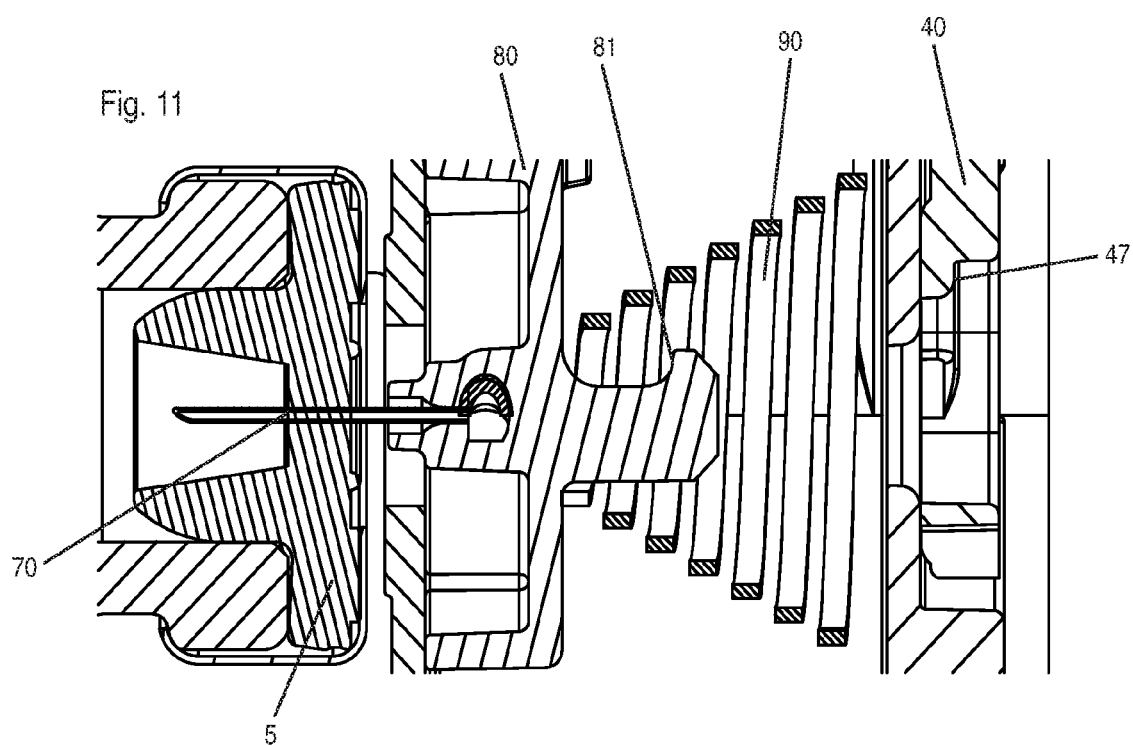
FIG. 11 illustrates a cross-sectional view of the spike carrier in a second position.

The control element 40 is engaged with the spike carrier 80, when the control element 40 is in its starting position. Thereby, the spike carrier 80 is retained in its first position and the spring 90 is prevented from expanding. Particularly, the control element 40 comprises a retaining surface 47 which engages a counter surface 81 to prevent the spike carrier 80 from being moved from the first position to the second position. By moving the control element 40 from its starting position in the first direction, e.g., the direction to the injection release position the control element 40 is disengaged from the spike carrier 80, particularly the retaining surface 47 disengages from the counter surface 81 such that the spike carrier 80 is free to be moved from the first position to the second position (FIG. 10). The spring 90 expands and thereby drives the spike carrier 80 from the first position into the second position (FIG. 11). The needle insertion and retraction mechanism 3 can be adapted such that the spike carrier 80 is released before, after or at the same time the needle carrier 20 is released to be moved in the needle insertion direction.

The spike carrier 80 comprises a main body which holds the spike 70 and which is linearly guided by the housing 10. The spike may be a hollow steel needle or made from a suitable plastic material. A hollow steel needle may be glued into the spike carrier 80. The spike carrier 80 comprises a protrusion which protrudes from the main body opposite to the direction in which the spike 70 protrudes. The protrusion extends through the (conical) helical spring 90, through a section of the housing 10. The section of the housing 10 can be arranged between the section of the control element 40 which comprises the retaining surface 47, and the spike carrier 80. The protrusion comprises the counter surface 81.

| LIST OF REFERENCE SIGNS | |
|---|---|
| 1 | drive module |
| 2 | needle insertion and retraction module |
| 3 | needle insertion and retraction mechanism |
| 4 | product container |
| 5 | pierceable wall/septum |
| 10 | housing |
| 11 | first housing |
| 11a | axial stop |
| 11b | stop surface |
| 11c | first longitudinal groove |
| 11d | second longitudinal groove |
| 12 | second housing |
| 13 | linear guide |
| 14 | linear guide |
| 15 | drive shaft |
| 16 | gear wheel |
| 17 | coupling member |
| 20 | needle carrier |
| 20c | first rib |
| 20d | second rib |
| 21 | counter stop surface |
| 22 | stop surface |
| 23 | stop surface |
| 25 | needle |
| 30 | spring/lever spring |
| 31 | first spring member |
| 31a | first spring arm |
| 31a' | first spring arm edge |
| 31b | first helical spring section |
| 32 | second spring member |
| 32a | second spring arm |
| 32a' | second spring arm edge |
| 32b | second helical spring section |
| 33 | interconnecting section |
| 40 | control element |
| 41 | gear rack |
| 42 | cap |
| 43 | main body |
| 44 | (first) stop surface |
| 45 | linear guide |
| 46 | linear guide |
| 47 | retaining surface |
| 50 | first intermediate member |
| 51 | counter stop surface |
| 60 | second intermediate member |
| 61 | counter stop surface |
| 70 | hollow spike |
| 80 | spike carrier |
| 81 | counter surface |
| 85 | flexible tube |
| 90 | spring |

What is claimed is:

1. A needle insertion and retraction mechanism for a medication delivery device for delivering a medicament, comprises:
   a housing;
   a needle carrier holding a needle, the needle carrier configured to be linearly guided by the housing along a longitudinal axis of the needle in a needle insertion direction and a needle retraction direction, which is opposite to the needle insertion direction;
   a first spring member configured to move the needle carrier with respect to the housing in the needle insertion direction;
   a second spring member, the second spring member being pre-loaded with stored energy sufficient to retract the needle carrier with respect to the housing in the needle retraction direction; and
   a control element configured to be linearly guided by the housing and moved transversely with respect to the longitudinal axis of the needle from a starting position, via a needle insertion release position, to a needle retraction release position,
   wherein:
   when the control element is in the starting position, the control element is operatively coupled to the needle carrier to prevent the needle carrier from being moved in the needle insertion direction,
   when the control element is in the needle insertion release position, the control element is decoupled from the needle carrier such that the first spring member drives the needle carrier in the needle insertion direction into a needle insertion position, while the second spring member is operatively coupled to the housing to keep the second spring member pre-loaded, and
   when the control element moves from the needle insertion release position to the needle retraction release position, the control element causes the second spring member to be decoupled from the housing such that the stored energy is released and the pre-loaded second spring member drives the needle carrier in the needle retraction direction.

2. The needle insertion and retraction mechanism according to claim 1, wherein when the control element is in the starting position, the first spring member is pre-loaded with stored energy sufficient to move the needle carrier with respect to the housing in the needle insertion direction and operatively coupled to the needle carrier and/or the second spring member is decoupled from the needle carrier.

3. The needle insertion and retraction mechanism according to claim 2, wherein when the control element is in the needle retraction release position, the first spring member is decoupled from the needle carrier.

4. The needle insertion and retraction mechanism according to claim 1, wherein when the control element is in the needle retraction release position, the first spring member is decoupled from the needle carrier.

5. The needle insertion and retraction mechanism according to claim 1, further comprising a first intermediate member arranged between the first spring member and the needle carrier.

6. The needle insertion and retraction mechanism according to claim 5, wherein the first spring member comprises a spring arm and the first intermediate member comprises a convexly curved contact surface on which the spring arm of the first spring member rests such that the first spring member slides and/or rolls over the curved contact surface when the first spring member drives the first intermediate member together with the needle carrier into the needle insertion position.

7. The needle insertion and retraction mechanism according to claim 5, wherein the first spring member comprises a spring arm and a free end of the spring arm comprises an edge, wherein, when the needle carrier is in the needle insertion position, the edge contacts the first intermediate member to block or interfere with a movement of the needle carrier in the needle retraction direction when the first intermediate member is engaged with the needle carrier.

8. The needle insertion and retraction mechanism according to claim 5, wherein the first intermediate member is linearly guided by the control element in the needle insertion direction, and is movable together while the control element moves transversely with respect to the needle insertion direction.

9. The needle insertion and retraction mechanism according to claim 8, wherein by moving the control element transversely with respect to the needle insertion direction, the first intermediate member is operatively disengaged from the needle carrier, whereby the needle carrier is free to be moved in the needle retraction direction.

10. The needle insertion and retraction mechanism according to claim 8, further comprising a second intermediate member arranged between the second spring member and the needle carrier, wherein the second intermediate member is linearly guided by the control element in the needle retraction direction, and is movable together while the control element moves transversely with respect to the needle retraction direction.

11. The needle insertion and retraction mechanism according to claim 5, wherein the first intermediate member is operatively coupled to the needle carrier when the control element is in the starting position, and wherein by moving the control element transversely with respect to the needle insertion direction, the control member is operatively disengaged from the needle carrier such that the first spring member drives the first intermediate member and needle carrier in the needle insertion direction.

12. The needle insertion and retraction mechanism according to claim 11, wherein by moving the control element transversely with respect to the needle insertion direction, the first intermediate member is operatively disengaged from the needle carrier, whereby the needle carrier is free to be moved in the needle retraction direction.

13. The needle insertion and retraction mechanism according to claim 11, further comprising a second intermediate member arranged between the second spring member and the needle carrier, wherein the second intermediate member is engaged with the housing when the control element is in the starting position and/or in the needle insertion release position, wherein by moving the control element from the needle insertion release position transversely with respect to the needle retraction direction, the second intermediate member is operatively disengaged from the housing and operatively engaged with needle carrier such that the second spring member drives the second intermediate member and needle carrier in the needle retraction direction.

14. The needle insertion and retraction mechanism according to claim 5, further comprising a second intermediate member arranged between the second spring member and the needle carrier, wherein the second spring member comprises a spring arm and the second intermediate member comprises a convexly curved contact surface on which the spring arm of the second spring member rests such that the second spring member slides and/or rolls over such contact surface when the second spring member drives the second intermediate member together with the needle carrier in the needle retraction direction.

15. The needle insertion and retraction mechanism according to claim 5, further comprising a second intermediate member arranged between the second spring member and the needle carrier, wherein the second spring member comprises a spring arm, wherein a free end of the spring arm comprises an edge, and when the needle carrier is in the needle retraction position, the edge contacts the second intermediate member to block or interfere with a movement of the needle carrier in the needle insertion direction when the second intermediate member is engaged with the needle carrier.

16. A medication delivery device configured as an infusion device or an infusion pump, the medication delivery device comprising the needle insertion and retraction mechanism of claim 1.

17. A medication delivery device, comprising:
a needle insertion and retraction module comprising a needle insertion and retraction mechanism, the needle insertion and retraction mechanism comprising:
a housing;
a needle carrier holding a needle, the needle carrier configured to be linearly guided by the housing along a longitudinal axis of the needle in a needle insertion direction and a needle retraction direction, which is opposite to the needle insertion direction;
a first spring member configured to move the needle carrier with respect to the housing in the needle insertion direction;
a second spring member, the second spring member being pre-loaded with stored energy sufficient to retract the needle carrier with respect to the housing in the needle retraction direction; and
a control element configured to be linearly guided by the housing and moved transversely with respect to the longitudinal axis of the needle from a starting position, via a needle insertion release position, to a needle retraction release position,
wherein:
when the control element is in the starting position, the control element is operatively coupled to the needle carrier to prevent the needle carrier from being moved in the needle insertion direction,
when the control element is in the needle insertion release position, the control element is decoupled from the needle carrier such that the first spring member drives the needle carrier in the needle insertion direction into a needle insertion position, while the second spring member is operatively coupled to the housing to keep the second spring member pre-loaded, and
when the control element moves from the needle insertion release position to the needle retraction release position, the control element causes the second spring member to be decoupled from the housing such that the stored energy is released and the pre-loaded second spring member drives the needle carrier in the needle retraction direction, and
wherein the needle insertion and retraction module is adapted to be operably attached to a motor of a drive module to cause the control element to move transversely with respect to the longitudinal axis of the needle from the starting position via the needle insertion release position to the needle retraction release position.

* * * * *